United States Patent

Schweitzer et al.

(10) Patent No.: US 8,696,636 B2
(45) Date of Patent: *Apr. 15, 2014

(54) SURGICAL SEALING ELEMENT HOLDER FOR HOLDING A SURGICAL SEALING ELEMENT AND SURGICAL SEALING SYSTEM

(75) Inventors: Tom Schweitzer, Tuttlingen (DE); Rupert Mayenberger, Rielasingen (DE)

(73) Assignee: Aesculap AG, Tuttlingen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/483,431

(22) Filed: May 30, 2012

(65) Prior Publication Data

US 2012/0238957 A1 Sep. 20, 2012

Related U.S. Application Data

(63) Continuation of application No. 12/459,018, filed on Jun. 24, 2009, now Pat. No. 8,246,586.

(30) Foreign Application Priority Data

Jul. 9, 2008 (DE) .......................... 10 2008 033 375

(51) Int. Cl.
*A61M 5/178* (2006.01)
*A61B 17/34* (2006.01)

(52) U.S. Cl.
USPC ............ 604/167.03; 604/167.06; 604/167.01; 604/256; 606/185

(58) Field of Classification Search
USPC .......... 604/164.01, 167.01, 167.06, 264, 506, 604/513, 167.03; 606/167, 185
See application file for complete search history.

(56) References Cited

U.S. PATENT DOCUMENTS

| | | |
|---|---|---|
| 3,712,298 A | 1/1973 | Snowdon et al. |
| 3,845,766 A | 11/1974 | Zöller |
| 4,265,694 A | 5/1981 | Boretos et al. |
| 4,924,923 A | 5/1990 | Boehmer et al. |
| 4,929,235 A | 5/1990 | Merry et al. |
| 5,104,382 A | 4/1992 | Brinkerhoff et al. |

(Continued)

FOREIGN PATENT DOCUMENTS

| | | |
|---|---|---|
| CA | 2 504 540 | 4/2005 |
| DE | 43 03 026 | 8/1994 |

(Continued)

OTHER PUBLICATIONS

Aesculap brochure, "MIT-System, Multi Interchangeable Trocar-System", 3 pages (undated).

*Primary Examiner* — Nicholas Lucchesi
*Assistant Examiner* — Leah Stohr
(74) *Attorney, Agent, or Firm* — Lipsitz & McAllister, LLC

(57) ABSTRACT

In order to improve a surgical sealing element holder for holding a surgical sealing element of a surgical sealing system comprising a trocar with a trocar sleeve, the sealing element having an insertion opening which can be widened, such that a sealing element of the sealing system can be replaced in a simple and reliable manner and it is ensured that sealing in relation to a channel of the trocar sleeve is perfect at all times it is suggested that a holder sealing element be provided for sealing the sealing element holder with respect to an inner wall surface of the trocar sleeve. In addition, an improved surgical sealing system is provided.

19 Claims, 15 Drawing Sheets

(56) References Cited

U.S. PATENT DOCUMENTS

| | | |
|---|---|---|
| 5,114,407 A | 5/1992 | Burbank |
| 5,127,626 A | 7/1992 | Hilal et al. |
| 5,141,498 A | 8/1992 | Christian |
| 5,152,754 A | 10/1992 | Plyley et al. |
| 5,174,613 A | 12/1992 | Joug |
| 5,180,373 A | 1/1993 | Green et al. |
| 5,197,955 A | 3/1993 | Stephens et al. |
| 5,203,773 A | 4/1993 | Green |
| 5,209,737 A | 5/1993 | Ritchart et al. |
| 5,256,147 A | 10/1993 | Vidal et al. |
| 5,261,891 A | 11/1993 | Brinkerhoff et al. |
| 5,267,965 A | 12/1993 | Deniega |
| 5,269,763 A | 12/1993 | Boehmer et al. |
| 5,295,993 A | 3/1994 | Green |
| 5,304,143 A | 4/1994 | Green et al. |
| 5,308,336 A | 5/1994 | Hart et al. |
| 5,314,417 A | 5/1994 | Stephens et al. |
| 5,318,585 A | 6/1994 | Guy et al. |
| 5,330,437 A | 7/1994 | Durman |
| 5,338,305 A | 8/1994 | Plyley et al. |
| 5,342,315 A | 8/1994 | Rowe et al. |
| 5,342,382 A | 8/1994 | Brinkerhoff et al. |
| 5,346,459 A | 9/1994 | Allen |
| 5,356,421 A | 10/1994 | Castro |
| 5,385,553 A | 1/1995 | Hart et al. |
| 5,387,197 A | 2/1995 | Smith et al. |
| 5,399,167 A | 3/1995 | Deniega |
| 5,405,328 A | 4/1995 | Vidal et al. |
| 5,441,041 A | 8/1995 | Sauer et al. |
| 5,441,513 A | 8/1995 | Roth |
| 5,462,532 A | 10/1995 | Gresl |
| 5,467,762 A | 11/1995 | Sauer et al. |
| 5,474,539 A | 12/1995 | Costa et al. |
| 5,476,475 A | 12/1995 | Gadberry |
| 5,486,190 A | 1/1996 | Green |
| 5,522,833 A | 6/1996 | Stephens et al. |
| 5,534,009 A | 7/1996 | Lander |
| 5,569,160 A | 10/1996 | Sauer et al. |
| 5,569,292 A | 10/1996 | Scwemberger et al. |
| 5,584,850 A | 12/1996 | Hart et al. |
| 5,603,702 A | 2/1997 | Smith et al. |
| 5,609,604 A | 3/1997 | Schwemberger et al. |
| 5,618,297 A | 4/1997 | Hart et al. |
| 5,626,598 A | 5/1997 | Roth |
| 5,658,236 A | 8/1997 | Sauer et al. |
| 5,662,615 A | 9/1997 | Blake, III |
| 5,669,885 A | 9/1997 | Smith |
| 5,685,854 A | 11/1997 | Green et al. |
| 5,690,663 A | 11/1997 | Stephens |
| 5,690,664 A | 11/1997 | Sauer et al. |
| 5,709,671 A | 1/1998 | Stephens et al. |
| 5,752,938 A | 5/1998 | Flatland et al. |
| 5,776,112 A | 7/1998 | Stephens et al. |
| 5,782,812 A | 7/1998 | Hart et al. |
| 5,792,113 A | 8/1998 | Kramer et al. |
| 5,803,919 A | 9/1998 | Hart et al. |
| 5,807,338 A | 9/1998 | Smith et al. |
| 5,817,061 A | 10/1998 | Goodwin et al. |
| 5,851,216 A | 12/1998 | Allen |
| 5,860,996 A | 1/1999 | Urban et al. |
| 5,865,807 A * | 2/1999 | Blake, III ............ 604/167.06 |
| 5,879,332 A | 3/1999 | Schwemberger et al. |
| 5,895,377 A | 4/1999 | Smith et al. |
| 5,904,699 A | 5/1999 | Schwemberger et al. |
| 5,906,595 A | 5/1999 | Powell et al. |
| 5,916,232 A | 6/1999 | Hart |
| 5,947,930 A | 9/1999 | Schwemberger et al. |
| 5,980,493 A | 11/1999 | Smith et al. |
| 5,989,224 A | 11/1999 | Exline et al. |
| 5,997,510 A | 12/1999 | Schwemberger |
| 6,004,326 A | 12/1999 | Castro et al. |
| 6,197,041 B1 | 3/2001 | Shichman et al. |
| 6,319,266 B1 | 11/2001 | Stellon et al. |
| 6,497,716 B1 | 12/2002 | Green et al. |
| 6,551,282 B1 | 4/2003 | Exline et al. |
| 6,685,630 B2 | 2/2004 | Sauer et al. |
| 6,702,787 B2 | 3/2004 | Racenet et al. |
| 7,169,130 B2 | 1/2007 | Exline et al. |
| 7,390,317 B2 | 6/2008 | Taylor et al. |
| 7,438,702 B2 | 10/2008 | Hart et al. |
| 7,597,701 B2 | 10/2009 | Hueil et al. |
| 7,637,896 B2 | 12/2009 | Voegele et al. |
| 7,731,694 B2 | 6/2010 | Becker et al. |
| 7,785,294 B2 | 8/2010 | Hueil et al. |
| 7,811,225 B2 | 10/2010 | Sauer et al. |
| 7,842,014 B2 | 11/2010 | Schweitzer et al. |
| 8,137,318 B2 | 3/2012 | Schweitzer et al. |
| 2001/0042927 A1 | 11/2001 | Rock |
| 2002/0026207 A1 | 2/2002 | Stellon et al. |
| 2002/0156432 A1 | 10/2002 | Racenet et al. |
| 2003/0195541 A1 | 10/2003 | Exline et al. |
| 2004/0059297 A1 | 3/2004 | Racenet et al. |
| 2004/0106942 A1 | 6/2004 | Taylor et al. |
| 2004/0111060 A1 | 6/2004 | Racenet et al. |
| 2004/0162531 A1 | 8/2004 | Wenchell |
| 2004/0215209 A1 | 10/2004 | Almond et al. |
| 2004/0230161 A1 | 11/2004 | Zeiner |
| 2004/0260244 A1 | 12/2004 | Piechowicz et al. |
| 2005/0033342 A1 | 2/2005 | Hart et al. |
| 2005/0065543 A1 | 3/2005 | Kahle et al. |
| 2005/0070943 A1 | 3/2005 | Hueil et al. |
| 2005/0077688 A1 | 4/2005 | Voegele et al. |
| 2005/0077689 A1 | 4/2005 | Hueil |
| 2005/0107816 A1 | 5/2005 | Pingleton et al. |
| 2005/0131349 A1 | 6/2005 | Albrecht et al. |
| 2005/0203467 A1 | 9/2005 | O'Heeron et al. |
| 2005/0251191 A1 | 11/2005 | Taylor et al. |
| 2005/0288622 A1 | 12/2005 | Albrecht et al. |
| 2005/0288634 A1 | 12/2005 | O'Heeron et al. |
| 2006/0211992 A1 | 9/2006 | Prosek |
| 2006/0217665 A1 | 9/2006 | Prosek |
| 2006/0229654 A1 | 10/2006 | Voegele et al. |
| 2006/0229655 A1 | 10/2006 | Voegele et al. |
| 2006/0264992 A1 | 11/2006 | Franer et al. |
| 2007/0088277 A1 | 4/2007 | McGinley et al. |
| 2007/0185453 A1 | 8/2007 | Michael et al. |
| 2007/0255218 A1 | 11/2007 | Faner |
| 2008/0154295 A1 | 6/2008 | Sauer et al. |
| 2008/0249475 A1 | 10/2008 | Albrecht et al. |
| 2008/0269696 A1 | 10/2008 | Exline et al. |
| 2009/0005739 A1 | 1/2009 | Hart et al. |
| 2009/0082735 A1 | 3/2009 | Schweitzer et al. |
| 2010/0106176 A1 | 4/2010 | Voegele et al. |
| 2010/0160938 A9 | 6/2010 | Franer et al. |
| 2011/0040255 A1 | 2/2011 | Schweitzer et al. |

FOREIGN PATENT DOCUMENTS

| | | |
|---|---|---|
| DE | 692 22 688 | 3/1998 |
| DE | 696 02 111 | 8/1999 |
| DE | 693 23 750 | 10/1999 |
| DE | 102 14 552 | 10/2003 |
| DE | 20 2006 005 442 | 7/2006 |
| DE | 698 38 231 | 5/2008 |
| EP | 0 426 407 | 5/1991 |
| EP | 0 474 124 | 3/1992 |
| EP | 0 495 633 | 7/1992 |
| EP | 0 495 634 | 7/1992 |
| EP | 0 552 851 | 7/1993 |
| EP | 0 350 291 | 9/1994 |
| EP | 0 312 219 | 12/1994 |
| EP | 0 479 130 | 12/1994 |
| EP | 0 520 296 | 4/1995 |
| EP | 0 494 520 | 9/1995 |
| EP | 0 511 676 | 7/1996 |
| EP | 0 499 457 | 5/1997 |
| EP | 0 567 142 | 7/1997 |
| EP | 0 517 248 | 10/1997 |
| EP | 0 617 924 | 10/1997 |
| EP | 0807416 | 11/1997 |
| EP | 0 642 764 | 12/1997 |
| EP | 0 630 213 | 1/1998 |
| EP | 0 594 687 | 4/1998 |
| EP | 0 600 921 | 5/1998 |

(56) References Cited

FOREIGN PATENT DOCUMENTS

| | | |
|---|---|---|
| EP | 0 649 634 | 9/1998 |
| EP | 0 697 838 | 9/1998 |
| EP | 0 630 619 | 10/1998 |
| EP | 0 648 096 | 11/1998 |
| EP | 0 696 459 | 11/1998 |
| EP | 0 768 063 | 2/1999 |
| EP | 0 652 730 | 3/1999 |
| EP | 0 724 864 | 4/1999 |
| EP | 0 591 851 | 6/1999 |
| EP | 0 684 016 | 12/1999 |
| EP | 0 768 064 | 12/1999 |
| EP | 0 604 197 | 2/2000 |
| EP | 0 614 384 | 2/2000 |
| EP | 0 701 799 | 3/2000 |
| EP | 0 716 862 | 8/2001 |
| EP | 0 994 740 | 7/2003 |
| EP | 0 785 756 | 9/2003 |
| EP | 1 058 566 | 10/2003 |
| EP | 0 769 278 | 1/2004 |
| EP | 0 807 414 | 1/2004 |
| EP | 1 402 827 | 3/2004 |
| EP | 1 459 688 | 9/2004 |
| EP | 0 867 150 | 11/2004 |
| EP | 1 350 476 | 4/2005 |
| EP | 1 520 539 | 4/2005 |
| EP | 1 520 541 | 4/2005 |
| EP | 0 873 721 | 12/2005 |
| EP | 1 625 863 | 2/2006 |
| EP | 1 671 596 | 6/2006 |
| EP | 1 707 136 | 10/2006 |
| EP | 1 707 137 | 10/2006 |
| EP | 1 716 813 | 11/2006 |
| EP | 1 520 544 | 6/2007 |
| EP | 1 582 158 | 12/2007 |
| EP | 1 889 580 | 2/2008 |
| GB | 1 466 242 | 3/1977 |
| WO | WO 93/01850 | 2/1993 |
| WO | WO 93/04632 | 3/1993 |
| WO | WO 93/04715 | 3/1993 |
| WO | WO 95/07663 | 3/1995 |
| WO | WO 95/15189 | 6/1995 |
| WO | WO 96/11640 | 4/1996 |
| WO | WO 98/50093 | 11/1998 |
| WO | WO 99/12481 | 3/1999 |
| WO | WO 99/52577 | 10/1999 |
| WO | WO 00/54679 | 9/2000 |
| WO | WO 01/89397 | 11/2001 |
| WO | WO 02/41795 | 5/2002 |
| WO | WO 03/026512 | 4/2003 |
| WO | WO 03/043683 | 5/2003 |
| WO | WO 03/096879 | 11/2003 |
| WO | WO 2004/096295 | 11/2004 |
| WO | WO 2005/032348 | 4/2005 |
| WO | WO 2005/053783 | 6/2005 |
| WO | WO 2005/060844 | 7/2005 |
| WO | WO 2005/112799 | 12/2005 |
| WO | WO 2006/004652 | 1/2006 |
| WO | WO 2006/119197 | 11/2006 |
| WO | WO 2007/098495 | 8/2007 |
| WO | WO 2007/110371 | 10/2007 |
| WO | WO 2007/121425 | 10/2007 |

* cited by examiner

236

SURGICAL SEALING ELEMENT HOLDER FOR HOLDING A SURGICAL SEALING ELEMENT AND SURGICAL SEALING SYSTEM

This application is a continuation of U.S. patent application Ser. No. 12/459,018 filed on Jun. 24, 2009, which claims priority from German patent application no. 10 2008 033 375.1 filed on Jul. 9, 2008, each of which is incorporated herein by reference in its entirety and for all purposes.

FIELD OF THE INVENTION

The present invention relates to surgical sealing element holders generally, and more specifically to a surgical sealing element holder for holding a surgical sealing element of a surgical sealing system comprising a trocar with a trocar sleeve, the sealing element having an insertion opening which can be widened.

Furthermore, the present invention relates to surgical sealing systems generally, and more specifically to a surgical sealing system comprising a trocar with a trocar sleeve and a surgical sealing element holder for holding a surgical sealing element which has an insertion opening which can be widened.

BACKGROUND OF THE INVENTION

A surgical sealing element holder as well as a surgical sealing system of the type described at the outset are known, for example, from DE 20 2006 005 442 U1. Sealing systems of this type are normally designed so as to be reusable as a whole or in part. Increased wear and tear can occur, in particular, in the case of sealing units of the sealing system on account of the insertion of instruments and so they can pass through only a limited number of reprocessing cycles, i.e., in particular, cleaning and subsequent sterilization. It is important, in particular, in the case of systems which can be reused only partially that the sealing element can be replaced in a simple and reliable manner and a channel defined by the trocar sleeve can be sealed securely against gas loss.

Therefore, it would be desirable to provide a surgical sealing element holder and a surgical sealing system of the type described at the outset which allow replacement of a sealing element of the sealing system in a simple and reliable manner and which ensure that sealing in relation to a channel of the trocar sleeve is perfect at all times.

SUMMARY OF THE INVENTION

In a first aspect of the invention, a surgical sealing element holder for holding a surgical sealing element of a surgical sealing system comprises a trocar with a trocar sleeve. The sealing element has an insertion opening adapted to be widened. The surgical sealing element holder comprises a holder sealing element for sealing the sealing element holder with respect to an inner wall surface of the trocar sleeve.

In a second aspect of the invention, a surgical sealing system comprises a trocar with a trocar sleeve and a surgical sealing element holder for holding a surgical sealing element having an insertion opening adapted to be widened. The sealing element holder has a holder sealing element for sealing the sealing element holder with respect to an inner wall surface of the trocar sleeve

BRIEF DESCRIPTION OF THE DRAWINGS

The foregoing summary and the following description may be better understood in conjunction with the drawing figures, of which.

DETAILED DESCRIPTION

Figure 1:
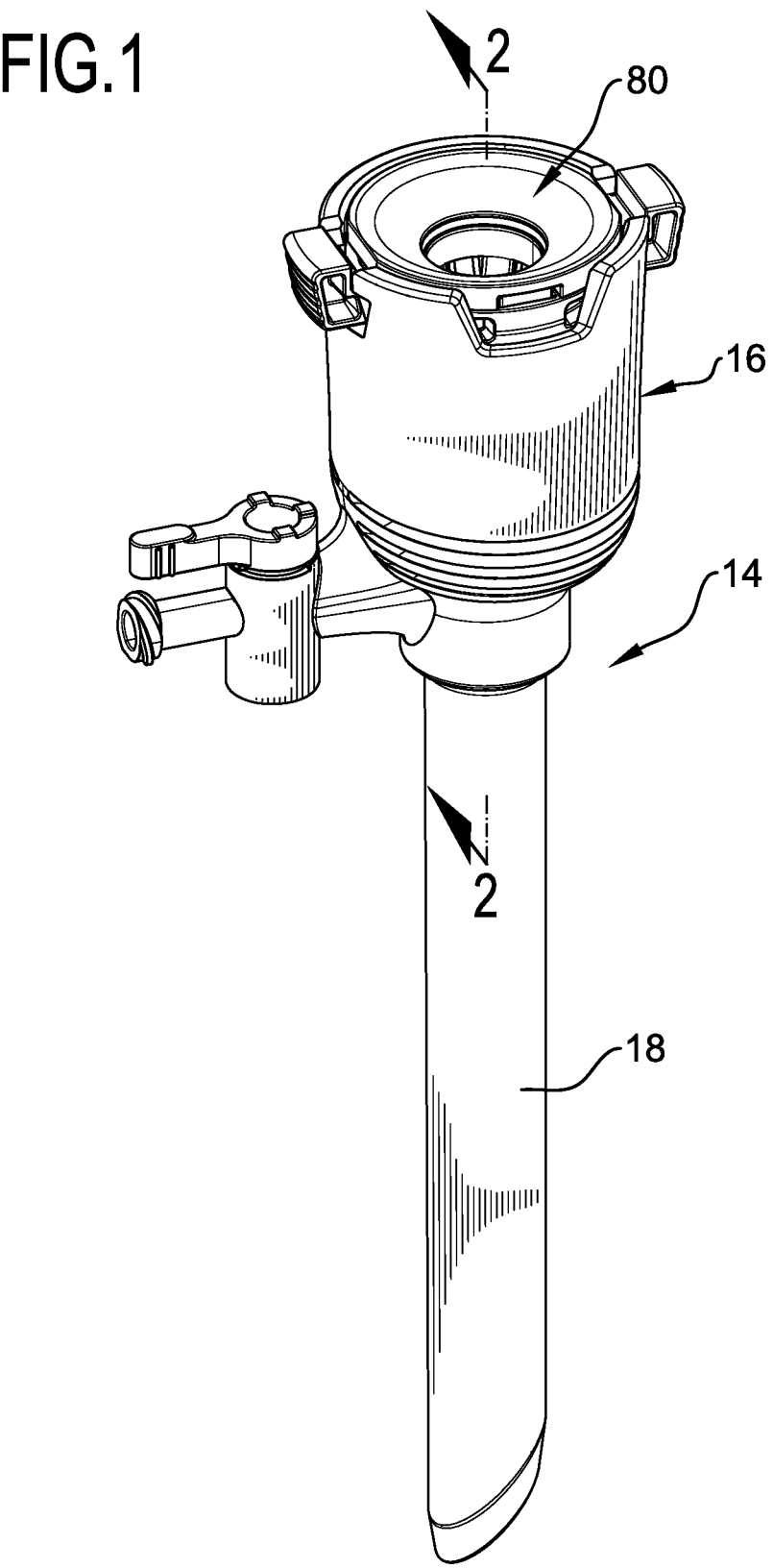
FIG. 1 shows a perspective overall view of a surgical sealing system.
Figure 2:
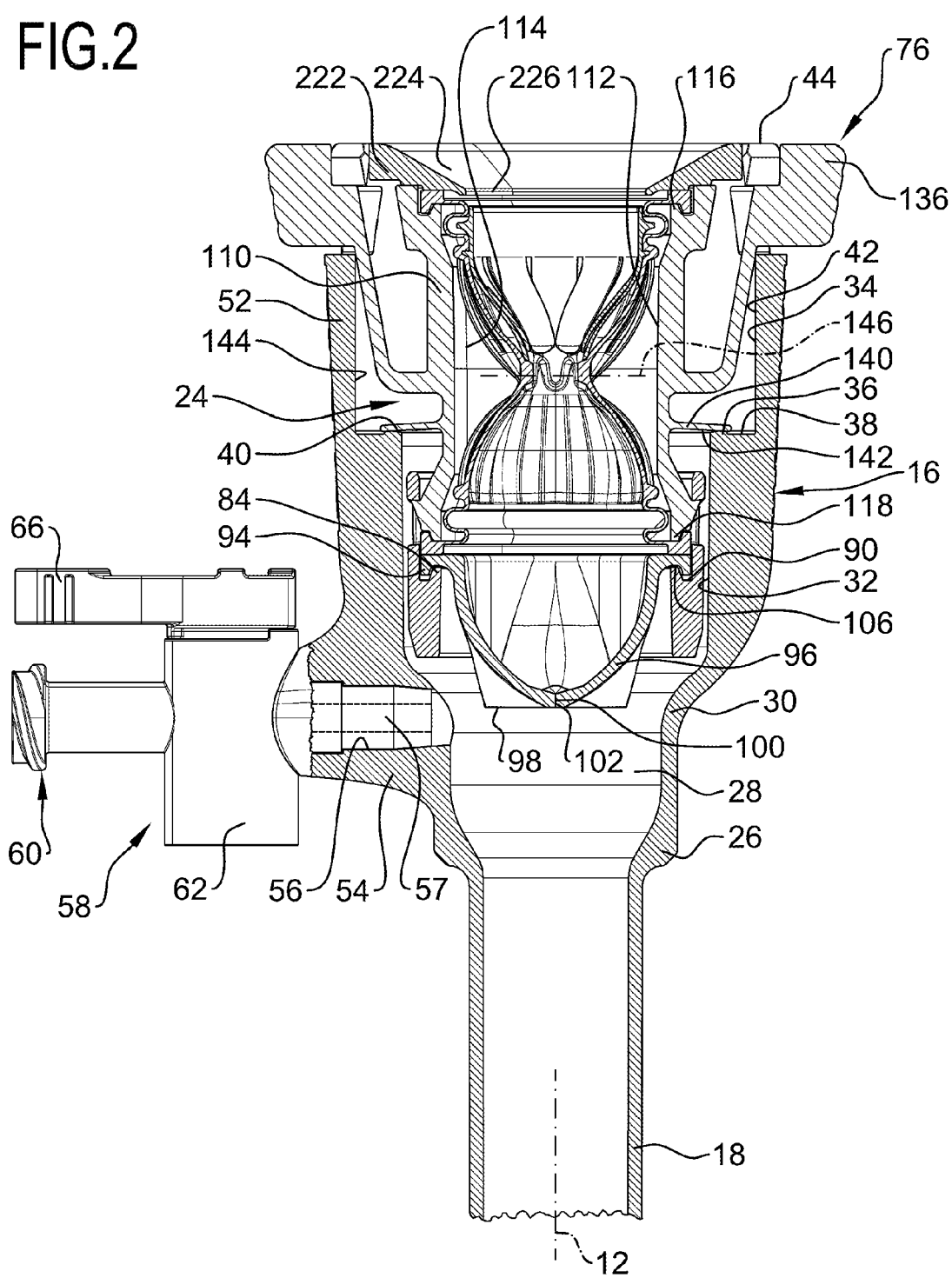
FIG. 2 shows a sectional view along line 2-2 in FIG. 1.

Although the invention is illustrated and described herein with reference to specific embodiments, the invention is not intended to be limited to the details shown. Rather, various modifications may be made in the details within the scope and range of equivalents of the claims and without departing from the invention.

The present invention relates to a surgical sealing element holder for holding a surgical sealing element of a surgical sealing system comprising a trocar with a trocar sleeve, said sealing element having an insertion opening adapted to be widened, comprising a holder sealing element for sealing the sealing element holder with respect to an inner wall surface of the trocar sleeve.

Losses of fluid, in particular, losses of gas through the sealing system can be prevented in a simple manner by the holder sealing element. An instrument insertion channel defined by the trocar sleeve can thus be sealed in an optimum manner, on the one hand, by the holder sealing element and, on the other hand, in particular, by a sealing element inserted into the sealing element holder. The sealing element holder has, in addition, the advantage that parts of the sealing system subject to wear, for example, the sealing element can, in particular, be replaced in a simple manner. The holder sealing element can, in addition, ensure a clearance-free fixing of the sealing unit in the trocar sleeve or a seal housing thereof. In addition, manufacturing tolerances for the sealing element holder and/or the trocar sleeve may be compensated by the holder sealing element in a simple and reliable manner. No further sealing elements are required to seal the sealing element holder relative to the trocar sleeve. This simplifies not only the assembling but also the disassembling of the sealing element holder from the trocar sleeve. In addition, costs of the sealing system can also be reduced as a whole since the holder sealing element, for example, can be integrated directly into the sealing element holder.

The sealing element holder is favorably designed for the detachable connection to the trocar sleeve. This allows the sealing element holder with a sealing element arranged thereon to be replaced quickly, easily and reliably.

The sealing element holder will be particularly simple in its construction as well as in its production when the holder sealing element is designed in the form of a flange which projects from the sealing element holder in a radial direction. The holder sealing element may thus be integrated directly into the sealing element holder.

Manufacturing tolerances may be compensated by the sealing element holder particularly well when the flange is inclined somewhat in a distal direction with respect to a plane which extends transversely to a longitudinal axis of the sealing element holder. An angle of inclination can be in a range of 1° to 15°, preferably in a range of 1° to 8°. For the purpose of sealing, the flange can thus be deformed somewhat in a proximal direction after abutting on a corresponding sealing surface of the trocar sleeve and can, in particular, press against the sealing surface whilst subject to pretensioning in order to ensure a permanent seal. The compensation of manufacturing tolerances at the trocar sleeve and/or the sealing element holder can also be brought about in a simple manner.

The sealing element holder may be produced particularly easily and inexpensively when the holder sealing element is designed in one piece with the sealing element holder. The sealing element holder can, therefore, be produced, for example, from a plastic material by way of injection molding in one working step.

The holder sealing element is advantageously deformable elastically at least in sections. In this way, manufacturing tolerances can be compensated, in particular, in a simple manner. A flexible configuration of the holder sealing element which is axially somewhat resilient is also favorable. An elastic deformability in sections is to be understood, in particular, as deformability along part of a radial extension of the holder sealing element.

It is favorable when the holder sealing element has an additional seal. Particularly when the holder sealing element itself is designed to be only slightly or even not elastic or flexible, the additional seal makes it possible to realize an optimum seal relative to the trocar sleeve. The additional seal is preferably designed in such a manner that it abuts on a corresponding sealing surface of the trocar sleeve when the sealing element holder is connected to the trocar sleeve.

It is advantageous when the additional seal is connected non-detachably to the holder sealing element. In this way, it will be possible, in particular, to connect the sealing element holder to the trocar sleeve or remove it from the sleeve with only one hand. The additional seal is preferably integrally formed onto the holder sealing element, in particular, by injection molding. In this way, the sealing element holder can be produced in a simple and inexpensive manner.

A particularly good and reliable seal between the sealing element holder and the trocar sleeve can be achieved when the additional seal is produced from an elastomer.

Moreover, the invention relates to a surgical sealing system comprising a trocar with a trocar sleeve and a surgical sealing element holder for holding a surgical sealing element having an insertion opening adapted to be widened, wherein the sealing element holder has a holder sealing element for sealing the sealing element holder with respect to an inner wall surface of the trocar sleeve.

Losses of fluid, in particular, losses of gas through the sealing system can be prevented in a simple manner by the holder sealing element. An instrument insertion channel defined by the trocar sleeve can thus be sealed in an optimum manner, on the one hand, by the holder sealing element and, on the other hand, in particular, by a sealing element inserted into the sealing element holder. The sealing element holder has, in addition, the advantage that parts of the sealing system subject to wear, for example, the sealing element can, in particular, be replaced in a simple manner. The holder sealing element can, in addition, ensure a clearance-free fixing of the sealing unit in the trocar sleeve or a seal housing thereof. In addition, manufacturing tolerances for the sealing element holder and/or the trocar sleeve may be compensated by the holder sealing element in a simple and reliable manner. No further sealing elements are required to seal the sealing element holder relative to the trocar sleeve. This simplifies not only the assembling but also the disassembling of the sealing element holder from the trocar sleeve. In addition, costs of the sealing system can also be reduced as a whole since the holder sealing element, for example, can be integrated directly into the sealing element holder.

It is particularly advantageous when the sealing element holder of the sealing system is one of the sealing element holders described above. The handling and operation of the sealing system are also improved as a whole with such a sealing element holder in the manner respectively described above.

The sealing element holder can preferably be connected detachably to the trocar sleeve. This makes it possible for the sealing element holder, on which a surgical sealing element can, in particular, be held, to be released from the trocar sleeve in a simple manner when wear or damage occurs at the sealing element or the sealing element holder.

The trocar sleeve preferably has a sealing element holder receptacle for the insertion of the sealing element holder. It is thus possible to assemble the parts of the sealing system in a simple and reliable manner and, where required, to replace them again.

Sealing of the sealing element holder relative to the trocar sleeve can be brought about in a simple and reliable manner when the holder sealing element abuts on an annular surface of the trocar sleeve which points in a proximal direction or essentially in a proximal direction. As a result, it will, in particular, be possible in a simple way to connect the sealing element holder to the trocar sleeve or also release it from the sleeve again with only one hand. Such a one-handed operation is not possible precisely in the case of sealing elements acting in a radial direction, for example, in the case of sealing rings pushed onto an outer surface of the sealing element holder.

It is favorable when the annular surface has an additional seal. Particularly when the holder sealing element itself is designed to be only slightly or even not elastic or flexible, the additional seal makes it possible to realize an optimum seal relative to the sealing element holder, in particular, relative to the holder sealing element. The additional seal is preferably arranged in such a manner that it abuts on the holder sealing element when the sealing element holder is connected to the trocar sleeve.

It is advantageous when the additional seal is connected non-detachably to the annular surface. In this way, it will be possible, in particular, to connect the sealing element holder to the trocar sleeve or release it from the sleeve with only one hand. The additional seal is preferably integrally formed, in particular, injection molded onto the holder sealing element. In this way, the trocar sleeve can be produced in a simple and inexpensive manner.

A particularly good and reliable seal between the sealing element holder and the trocar sleeve can be achieved when the additional seal is produced from an elastomer.

The construction of the sealing system will be particularly simple when the annular surface is defined by a one-step narrowing of an inner diameter of the trocar sleeve. The narrowing of the diameter can be formed, in particular, in a direction towards a distal end of the trocar sleeve. It can, however, also be in steps or continuous and be inclined in relation to a plane which extends transversely to the longitudinal axis of the trocar sleeve, for example, through an angle of inclination in a range of 10° to 80°, preferably 30° to 60°.

In order to seal a shaft of an instrument, which can be inserted into the trocar, against any loss of gas when the instrument shaft passes through the trocar sleeve for a surgical procedure, it is favorable when the sealing system comprises a surgical sealing element, which is held on the sealing element holder and has an insertion opening which can be widened, for sealing the insertion opening during the insertion of a surgical instrument.

In addition, it is favorable when the sealing system comprises a surgical protection device for the sealing element, this protection device comprising a base member which can be arranged on the trocar or on a part thereof, is closed in a ring shape or closed essentially in a ring shape and has an opening and several protection elements which are arranged in circumferential direction and point parallel or towards a longitudinal axis of the protection device, these protection elements having free ends which point essentially in a distal direction, wherein at least some of the protection elements have at least one retaining element on their outer side at their free ends or in the area of their free ends for engagement with the sealing element. The protection elements of the protection device can cover an inner surface of the sealing element essentially completely so that, during the insertion of an instrument into the trocar sleeve, the instrument comes into contact, first of all, with the protection elements and expands them as required, wherein the protection elements then come into contact with the sealing element and can expand it. This enables damage to the sealing element caused by instruments inserted into the trocar sleeve to be avoided. To provide the retaining elements on at least some of the protection elements has the advantage that the protection device can specifically become caught in the sealing element which is precisely what should be avoided during the insertion of an instrument. During the insertion of instruments, the fact that the retaining elements are brought into engagement with the sealing element has the advantage that it is thus ensured that protection of the sealing element can be ensured as far as the area of the sealing element which abuts on the instrument shaft inserted, i.e., in particular, a defined sealing line or sealing lip. Due to the fact that the retaining elements are brought into engagement with the sealing element, any widening of the insertion opening of the protection device automatically leads to an expansion of the sealing element, as well. A relative movement between the protection device and the sealing element will, however, be essentially prevented. This has the advantage that a covering of the sealing element which is provided once the retaining elements are brought into engagement with the sealing element can be ensured in an axial direction of the protection device irrespective of an insertion position of the instrument applied. Engagement can be brought about, in particular, when the retaining element has a minimum diameter so that when it abuts on, for example, a sealing element produced from an elastomer it causes its wall to bulge and can thus, as it were, define a corresponding recess, in which the retaining element engages. As a result of this bulging, any sliding along the sealing element on the part of the object causing the sealing element to bulge will, however, be prevented. A single retaining element is preferably provided on the respective protection elements. In principle, it would also be conceivable to provide several retaining elements, i.e., two, three or more on each protection element in order to prevent any relative movement between the retaining elements and the sealing element when the sealing element is unfolded for the purpose of widening the insertion opening as a result of the retaining elements being brought into engagement with the sealing element.

It is favorable when the at least one retaining element is designed in the form of a retaining projection protruding from the respective protection element. Retaining elements of this type are particularly easy to produce and can be dimensioned accordingly in order to ensure a specific catching or otherwise engagement of the retaining projections in or with the sealing element.

Depending on orientation of the protection elements in a basic position or also a widened position, it is advantageous when at least some of the retaining projections protrude from the protection elements at right angles or essentially at right angles. In addition, such a configuration of the retaining projections is particularly simple to produce. Catching or engagement of the retaining projections in or with the sealing element can be improved, particularly when the protection elements project parallel to a longitudinal axis defined by the sealing element on the base member, when at least some of the retaining projections project away from the protection elements at an angle with respect to an extension of the protection elements in the area of their free ends. Retaining projections of this type point, in particular, away from the base member and outwards in the direction towards the sealing element. It can, therefore, be ensured that the retaining projections will become caught in the sealing element in a simple and reliable manner.

A trocar system provided altogether with the reference numeral 10 and forming a surgical sealing system is schematically illustrated in FIGS. 1 to 13. It comprises a trocar sleeve 14 which defines a longitudinal axis 12 and has a seal housing 16 and a shaft 18 extending away from it in a distal direction, a seal arrangement 20 arranged in the seal housing 16 as well as an obturator 22 which has a distal end especially formed for severing and expanding body tissue and is pushed into the trocar sleeve 14 prior to the insertion of the trocar sleeve 14 into the body of a patient in order to facilitate the insertion of the trocar sleeve 14 into the body of the patient.

The trocar sleeve 14 is designed to be essentially rotationally symmetric and defines a receptacle 24 for the seal arrangement 20 in the interior of the seal housing 16. A minimum inner diameter of the trocar sleeve 14 is defined by the shaft 18. In a first area of transition 26 from the shaft 18 to the seal housing 16, the inner diameter of the shaft 18 enlarges continuously and remains constant in the area of a first enlargement space 28. The first enlargement space 28 is adjoined by a second area of transition 30, in which the inner diameter of the trocar sleeve 14 again enlarges continuously as far as a distal part 32 of the receptacle 24.

Figure 3:
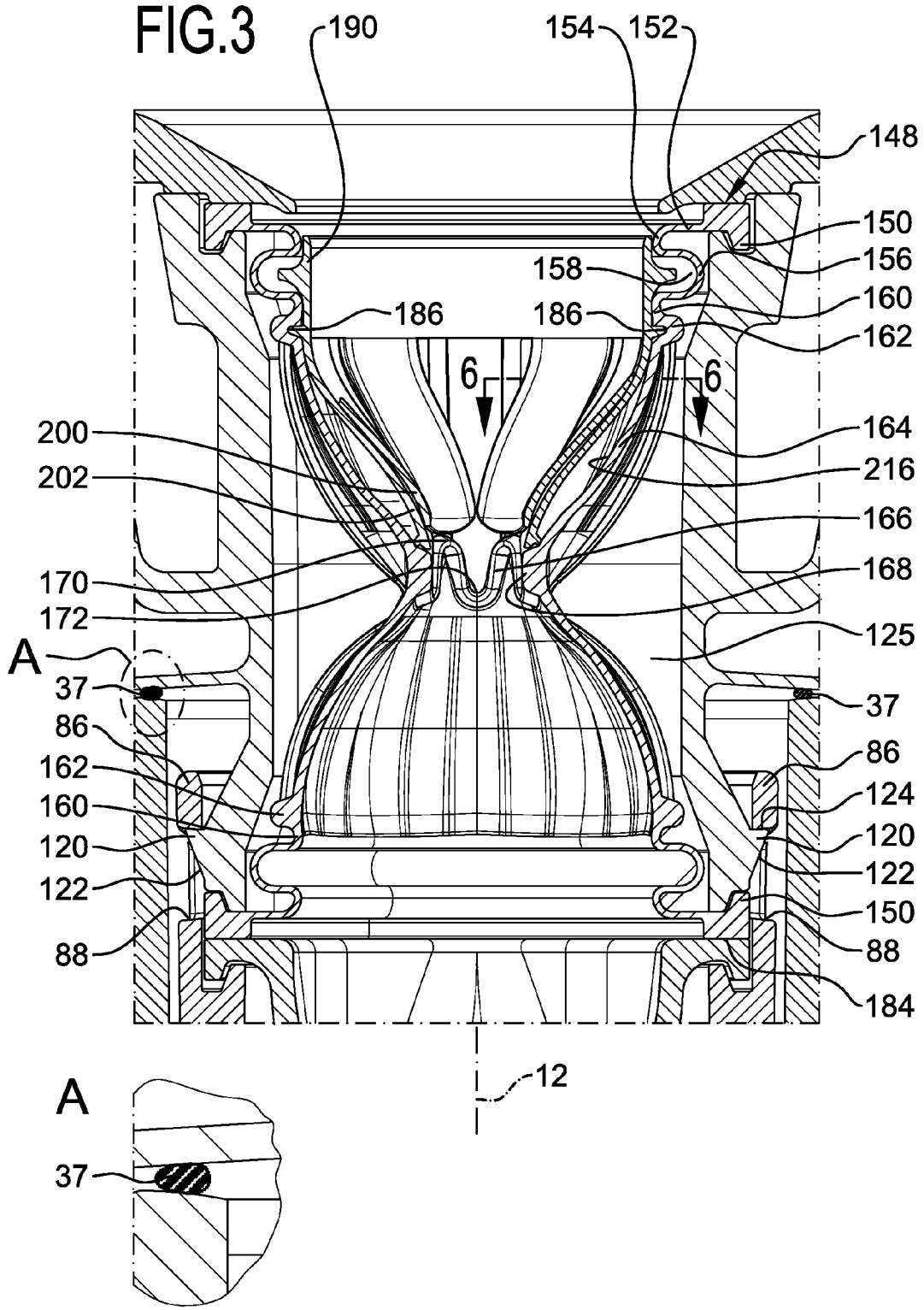
FIG. 3 shows an enlarged partial view of the sectional view in FIG. 2.
Figure 4:
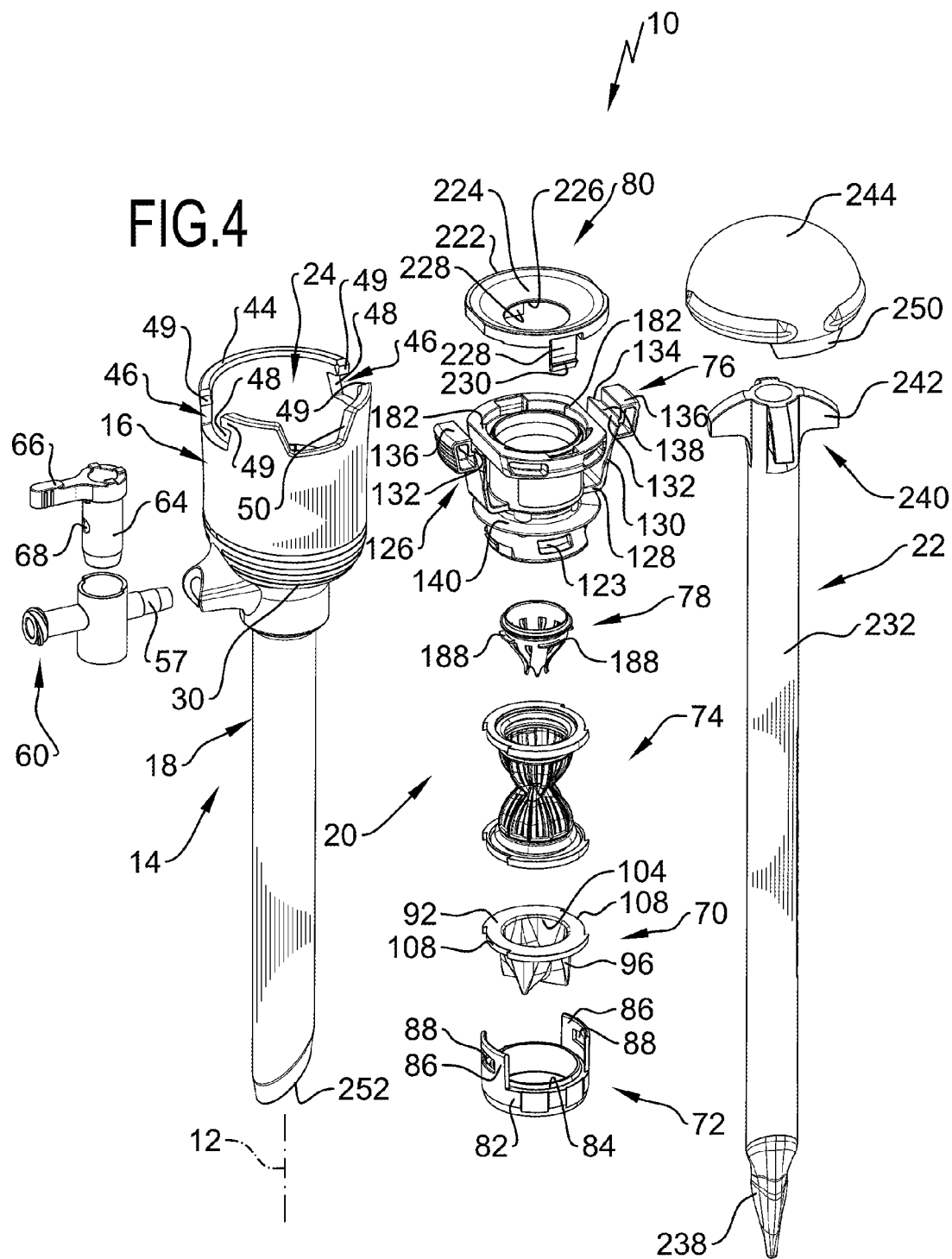
FIG. 4 shows a perspective, exploded illustration of the sealing system from FIG. 1.
Figure 5:
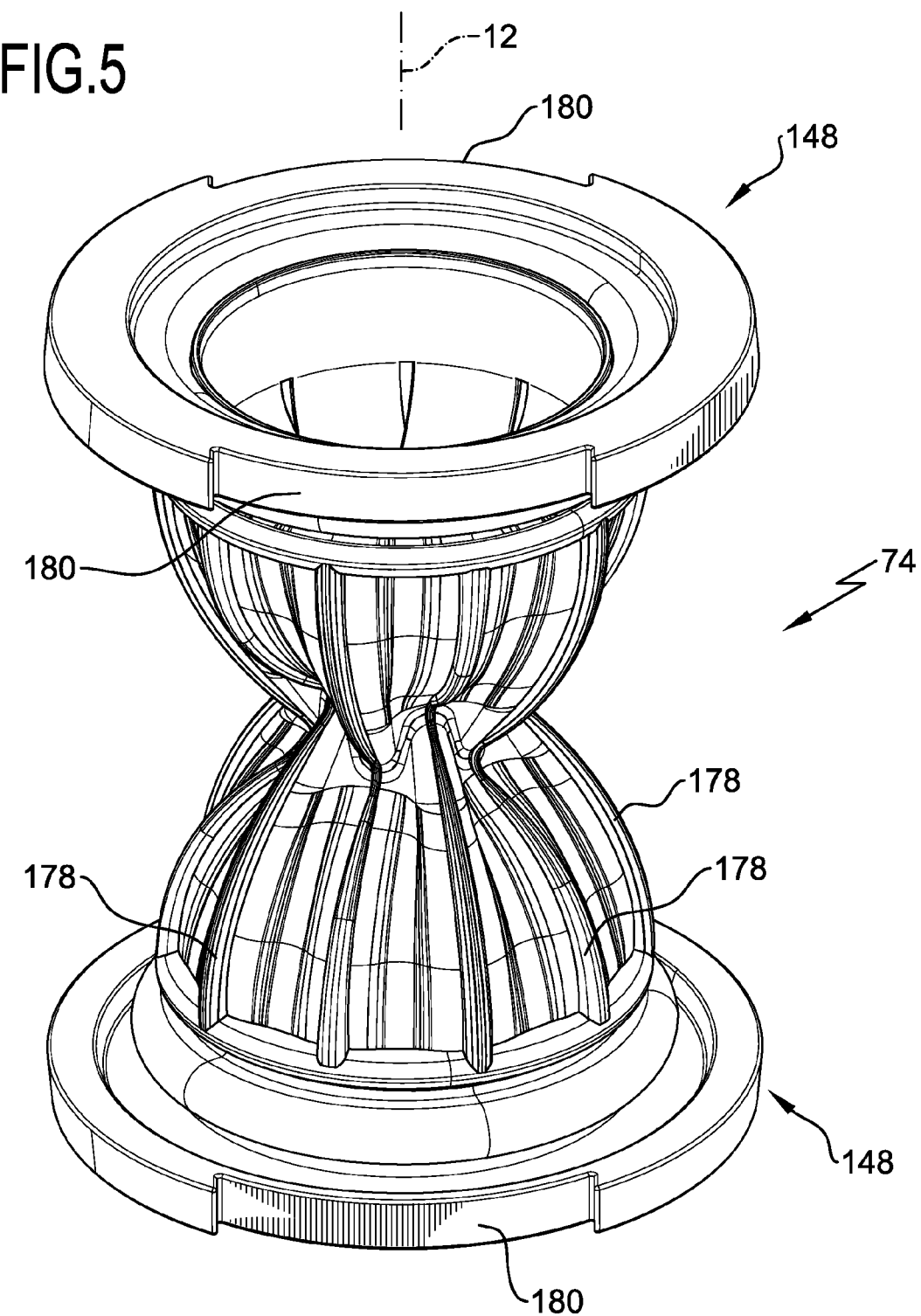
FIG. 5 shows a perspective view of the sealing element from FIG. 4.

An inner diameter of the seal housing 16 enlarges in one step during the transition from the distal part 32 to a proximal part 34 thereof so that an annular surface 36 is defined which points in a proximal direction. The annular surface can optionally bear an additional seal 37 which is produced by injection molding an elastomer and is illustrated in FIG. 3, for example, by dotted lines. A flat recess 38 in the annular surface therefore defines a flat sealing surface 40 which projects somewhat in a proximal direction and is separated from an inner wall 42 of the proximal part 34 by the recess 38.

Proceeding from a proximal end 44 of the seal housing 16, two locking receptacles 46 are formed, which are symmetric to one another, located diametrically opposite one another with respect to the longitudinal axis 12 and each have two lateral undercuts 48 which are open in directions opposite to one another in circumferential direction. The locking receptacles 46 form part of a snap-in connection, with which the seal arrangement 20 can be locked in the seal housing 16, as will be explained in detail in the following.

Figure 12:
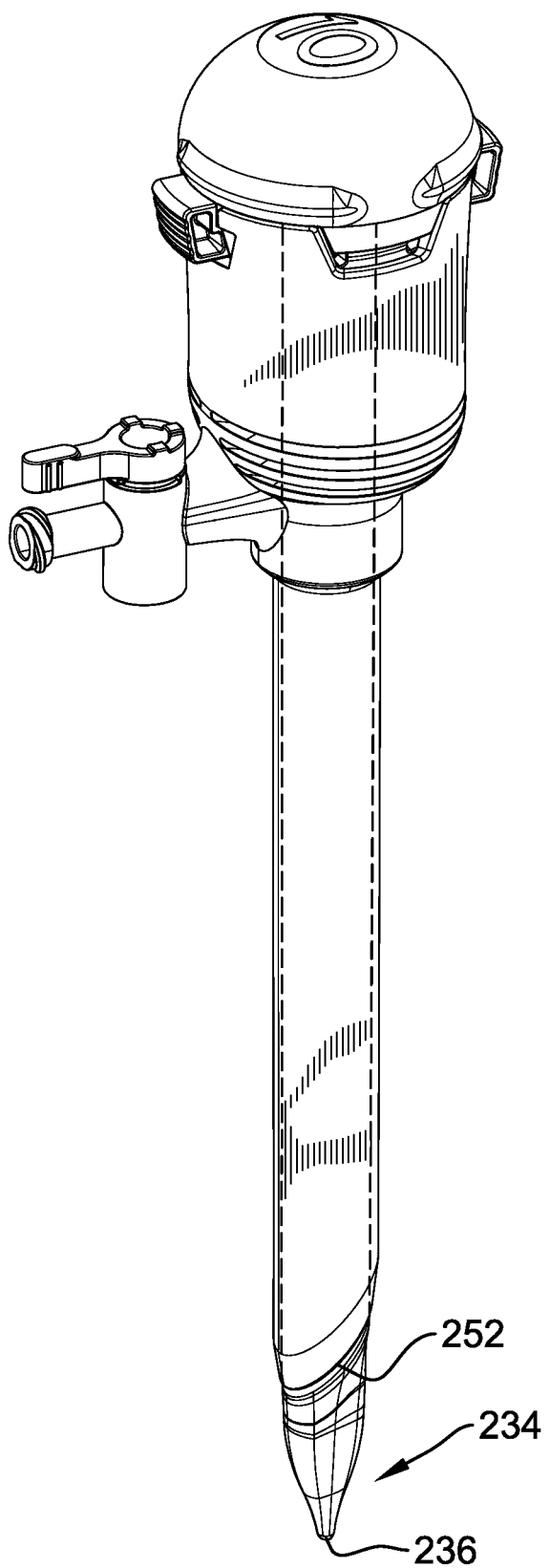
FIG. 12 shows a view analogous to FIG. 1 of the sealing system with obturator inserted.
Figure 13:
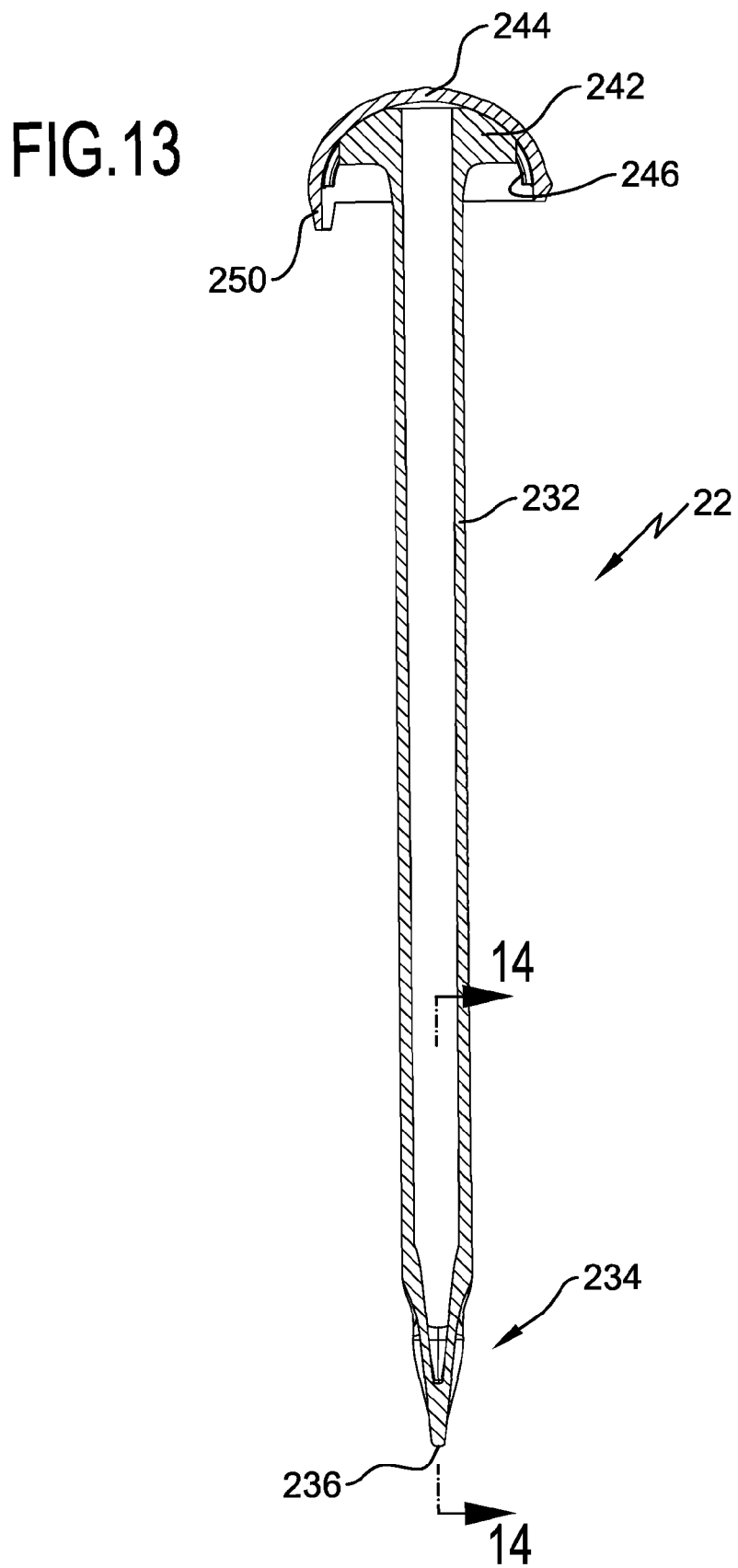
FIG. 13 shows a longitudinal, sectional view of the obturator illustrated in FIG. 12.
Figure 14:
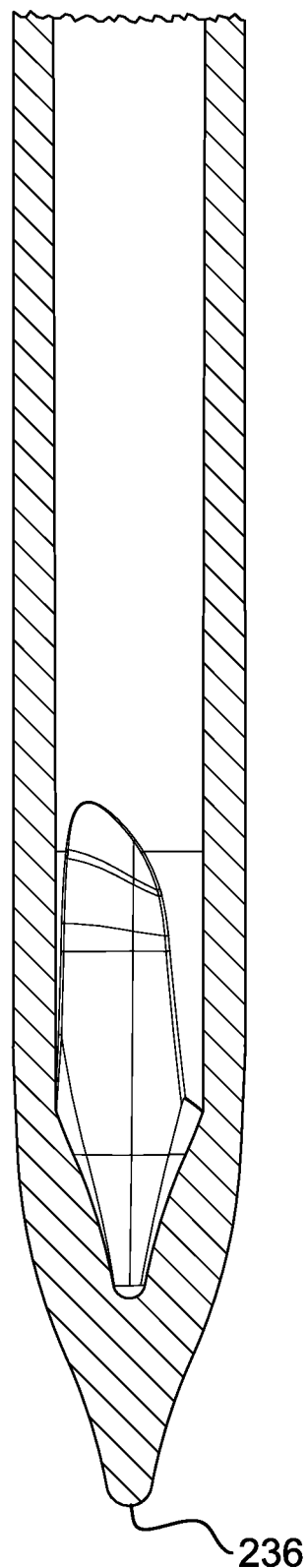
FIG. 14 shows a sectional view along line 14-14 in FIG. 13.

Furthermore, proceeding from the end 44, a recess 50 narrowing somewhat in a distal direction is formed symmetrically between the locking receptacles 46 in a wall 52 of the seal housing 16 and a corresponding projection 250 of the obturator 22 engages in the recess when the obturator 22 is inserted fully into the trocar sleeve 14, as illustrated in FIG. 12.

A short connection piece 54 is integrally formed on the seal housing 16 on one side in the area of the second area of transition 30 and defines a channel 56 which extends at right angles to the longitudinal axis 12. A connection piece 57 of a closure element 58 is pushed into the channel 56 and has a standardized Luer lock connection 60 which projects in an opposite direction.

The closure element 58 comprises a cylindrical valve housing 62, into which a cylindrical closing plunger 64 is inserted, which has a corresponding design and an actuating lever 66 integrally formed thereon. The closing plunger 64 is provided with a bore 68 so that the channel 56 for fluids can be opened or closed as a function of a rotary position of the closing plunger 64 relative to the valve housing 62. Instead of the closure element 58 described, other optional types of known closure elements can also be provided, in particular, also special, spring-loaded and, therefore, self-locking Luer lock connections.

The seal arrangement 20 comprises two seals, namely a cross recessed valve 70 which is held on a holder ring 72 as well as a sealing element 74 which is described in detail in its principal construction in German Utility Model 20 2006 005 442. The description in this publication is incorporated herewith into the present description in its entirety.

The sealing element 74 is held in the interior of a sealing element holder 76 which can be connected detachably to the holder ring 72. On the proximal side, a protection device 78 is detachably held on the sealing element 74 so that the sealing element 74 can be removed from the sealing element holder 76 together with the protection device 78 as required. On the proximal side, the sealing element holder 76 can be closed by a cover 80.

The individual parts of the seal arrangement 20 will be described in greater detail in the following.

The holder ring 72 comprises a ring 82 which is circular in cross section and from the edge of which on the proximal side an annular flange 84 is formed which projects in a proximal direction but does not extend over the entire width of a wall of the ring 82 but rather only over about half of it.

Furthermore, two connecting wings 86 designed symmetrically to one another project in a proximal direction from the proximal edge of the ring 82, located diametrically opposite one another with respect to the longitudinal axis 12. The connecting wings 86 each have two essentially rectangular openings 88 which are oriented transversely to the longitudinal axis 12. The connecting wings 86 are arranged at a certain distance from the flange 84 so that a groove 90 is formed between the flange 84 and each of the connecting wings 86.

The cross recessed valve 70 comprises, on the proximal side, an annular attachment flange 92 which has an annular projection 94 which points in a distal direction and is designed to correspond to the grooves 90 in its height as well as in its outer dimensions. The cross recessed valve 70 further comprises a valve member 96 which projects in a distal direction on the attachment flange 92 and opens on the distal side into a cross-shaped end surface 98 which is provided with two slits 100 at right angles to one another. The valve member 96 is designed in a basic position, as illustrated, for example, in FIGS. 2 and 4, such that the sectional surfaces 102 of the valve member 96 which are separated by the slits 100 abut directly on one another and thus close an annular opening 104 defined by the attachment flange 92 completely, somewhat on the distal side of the attachment flange 92. The valve member 96 is, on the proximal side, integrally formed directly on an inner edge of the attachment flange 92 so that an annular groove 106, in which the flange 84 can engage essentially in a form-locking manner, is formed between the valve member 96 and the annular projection 94.

The attachment flange 92 is provided, in addition, with two recesses 108, which point in a radial direction and in which the connecting wings 86 engage when the valve member 96 is inserted into the holder ring 72, and projects beyond an edge of the ring 82 on the distal side at least partially with the valve member 96, in particular, with its end surface 98 having the slits 100.

The sealing element holder 76 is of an essentially elongated, sleeve-like design. It comprises a central sleeve member 110 which is formed coaxially to the longitudinal axis 22. An inner surface 112 of the sleeve member 110 is designed to be completely rotationally symmetric. The inner surface 112 defines and delimits a longitudinal channel 114, into which the sealing element 74 is inserted. An inner diameter of the sleeve member 110 widens somewhat towards the respective distal and proximal ends thereof. Annular projections 116 and 118 are formed on the distal side and on the proximal side, respectively, and these point in a proximal and a distal direction, respectively, in order to be brought into engagement with corresponding flanges and grooves, respectively, on the sealing element 74.

Two snap-in noses 120 are formed on an outer side of the sleeve member 110 somewhat on the proximal side of the annular projection 118 on the distal side. These snap-in noses point in opposite directions, are located diametrically opposite one another with respect to the longitudinal axis 12 and define slide-on surfaces 122, which point outwardly and are inclined somewhat in a distal direction, and, therefore, also an annular edge 124 which points in a proximal direction. The snap-in noses 120 are designed to correspond to the openings 88 in the connecting wings 86. The connecting wings 86 can be pushed over the slide-on surfaces 122 from the distal side so that they pivot outwards somewhat in a radial direction away from the longitudinal axis 12. As soon as the snap-in noses 120 can engage fully in the openings 88, the connecting wings 86 spring back again in the direction towards the longitudinal axis 12. The holder ring 72 and the sealing element holder 76 can be interlockingly connected to one another in the manner described.

Two rectangular openings 123 are provided in the sleeve member 110 between the snap-in noses 120, i.e., offset through 90° relative to them in circumferential direction, these openings connecting an interior space 125 of the sleeve member 110 to an outer side thereof. In this way, a balance of pressure between the interior space 125 and the surroundings of the seal element holder 76 can be achieved. The balance of pressure which can be achieved in this way between a gas pressure prevailing in the body of a patient and the interior space 125 or the de-aeration/aeration of the interior space 125 thus possible prevents the sealing element 74 from having to widen against a gas volume in the interior space which would become trapped following assembly of the sealing element 74 on the sealing element holder 76.

In order to connect the sealing element holder 76 to the seal housing 16, two coupling members 126 are arranged so as to project from an outer side of the sealing element holder 76 and be located diametrically opposite one another. They each comprise a transverse web 128, which projects directly from the sleeve member 110 in a radial direction and away from which a spring part 130 extends which extends essentially parallel to the sleeve member 110 in a proximal direction. At a proximal end of the spring part 130, protruding snap-in projections 132 are formed on both sides of the spring part 130 pointing essentially in circumferential direction, these projections each defining slide-on surfaces 134 which point away from the longitudinal axis 12. An operating element 136 essentially in the shape of a parallelepiped is arranged on an outer side of the spring parts 130 between the slide-on surfaces 134 and projects somewhat beyond the end of the spring part 130 on the proximal side.

In order to connect the sealing element holder 76 to the seal housing 16, the distal end of the sealing element holder 76 is inserted into the seal housing 16 until the projections 49 which laterally delimit the undercuts 46 come into contact with the slide-on surfaces 134 and pivot the spring parts 130 somewhat in the direction towards the longitudinal axis 12 as a result of the sliding contact. As soon as a proximal end surface 138 of the spring parts 130 can engage in the undercut 48, the spring parts 130 spring outwards somewhat in a radial direction and the end surface 130 abuts on an edge of the projection 49 pointing in a distal direction. In order to release the sealing element holder 76 from the trocar sleeve 14, the operating elements 136 can be acted upon with a force acting in the direction towards the longitudinal axis 12 so that the spring parts 130 are pivoted in the direction towards the longitudinal axis 12 and the snap-in projections 132 again release the undercut 48. The sealing element holder 76 can then be withdrawn from the seal housing 16 in a proximal direction.

A holder sealing element 140 is formed somewhat to the distal side of the transverse webs 128, namely in the form of an annular flange which projects essentially in a radial direction and is inclined somewhat in a distal direction, namely through about 2° with respect to a transverse plane extending at right angles to the longitudinal axis 12. The holder sealing element 140 has a thickness which predetermines a certain elasticity or flexibility of the holder sealing element 140. It can, therefore, be somewhat elastic in an axial direction and compensate for manufacturing tolerances at the trocar sleeve 14 and the sealing element holder 76. The holder sealing element 140 is arranged on the sealing element holder 76 in such a manner that when the sealing element holder 76 is connected in a snap-in manner to the seal housing 16 in the manner described, a sealing surface 142 of the sealing element holder 76 which points in a distal direction abuts on the annular surface 36, optionally somewhat pretensioned, and thus a perfect sealing of the sealing element holder 76 is achieved with respect to an inner wall 144 of the seal housing 16 of the trocar sleeve. The holder sealing element 140 can optionally bear a further seal 141, which is produced by injection molding an elastomer and drawn in, by way of example, in FIG. 11 as dotted lines, for the purpose of improving the sealing effect.

Figure 11:
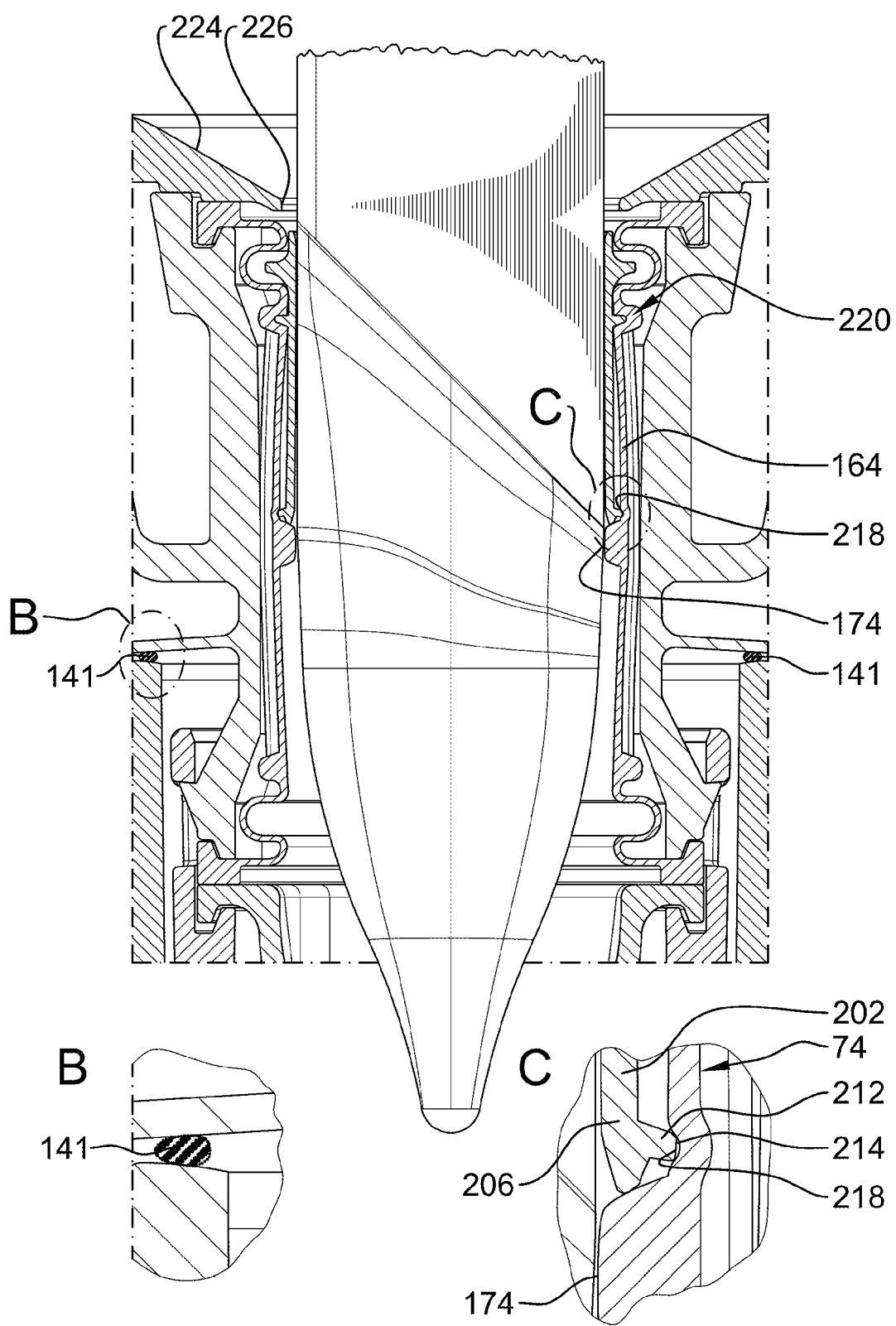
FIG. 11 shows a sectional view analogous to FIG. 3 during the insertion of an obturator of the sealing system.
Figure 15:
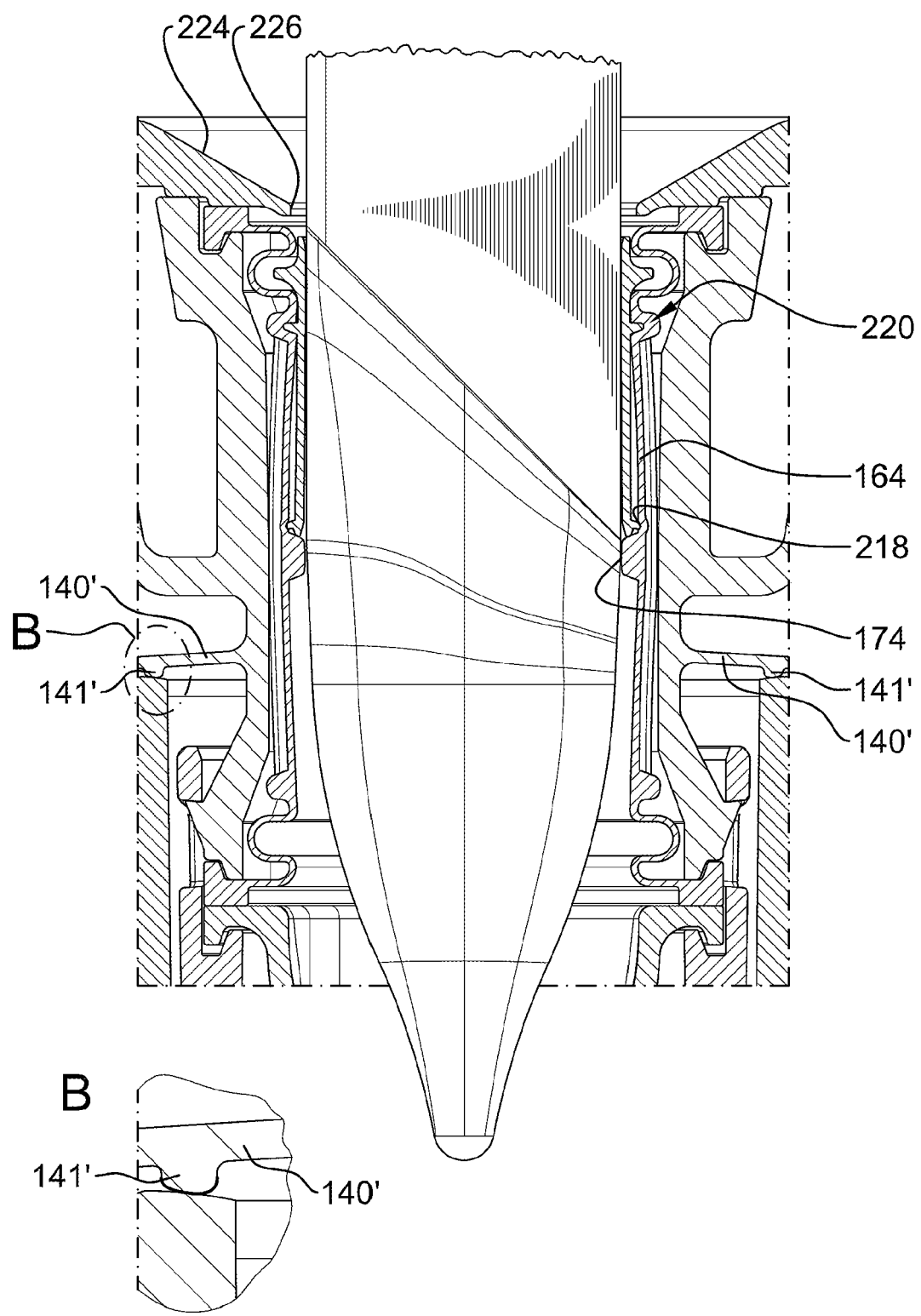
FIG. 15 shows a sectional view analogous to FIG. 11 during the insertion of an obturator of the sealing system.

As an alternative to the separate additional seal 141 shown in FIG. 11, FIG. 15 shows an example embodiment in which the additional seal 141' is integrally formed onto the holder sealing element 140', in particular, by injection molding. In this way, the sealing element holder can be produced in a simple and inexpensive manner.

The sealing element 74 is designed to be essentially rotationally symmetric with respect to the longitudinal axis 12. Furthermore, it is designed to be essentially mirror symmetric with respect to a plane of opening 146 which extends transversely to the longitudinal axis. The plane of opening 146 extends parallel to two flange rings 148 on both sides, which limit the sealing element 74 on the distal side and the proximal side and define a maximum outer diameter of the sealing element 74. Annular projections 150, which can engage around the annular projections 116 and 118 on the outside, project from the flange rings 148 as far to the outside on them as possible and each points in the direction of the other flange ring 148. The sealing element 74 can thus be suspended or tensioned in a simple manner via the annular projections 116 and 118 and held in the interior of the sealing element holder 76.

A first transverse section 152 extends from the flange rings 148 in a radial direction towards the longitudinal axis 12 and merges into a first bead section 154 which is bent back towards the outside and merges, on the other hand, directly into a second bead section 156 which has, on the other hand, an end directed towards the longitudinal axis 12. The second bead section 156 thus defines an annular groove 158 which is open in the direction towards the longitudinal axis.

Figure 6:
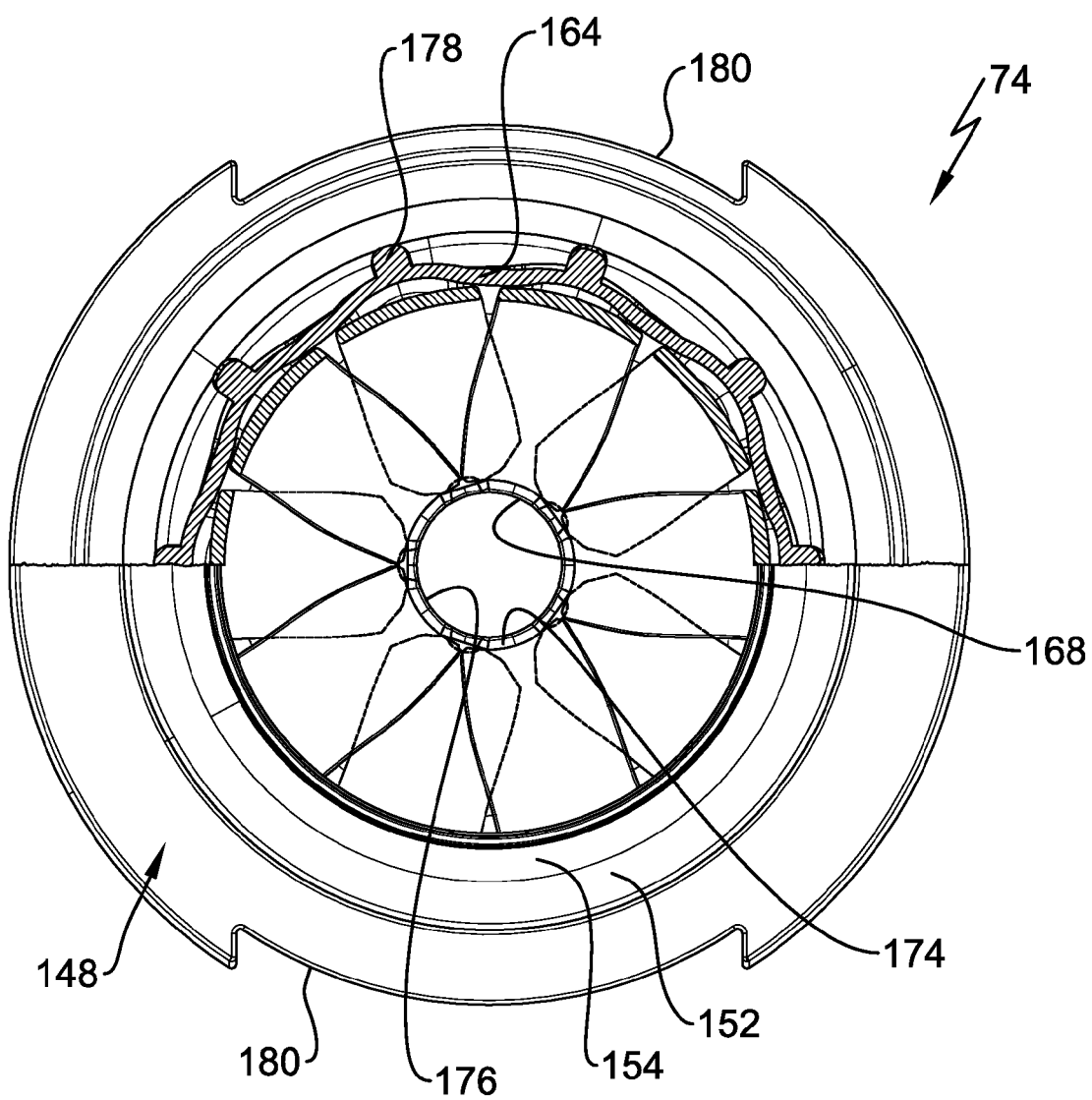
FIG. 6 shows a sectional view along line 6-6 in FIG. 3.

On the distal side, a short cylindrical section 160 adjoins the second bead section 156 and merges into a thickened bead 162 protruding outwards on the sealing element 74. Proceeding from the beads 162, at which a wall 164 of the sealing element 74 projects essentially without folds, the wall 164 is folded like curtains as far as the plane of opening 146. The folding results in a sealing line 166 which, in the form of a wave line, defines wave peaks 170 on the proximal side of the plane of opening 146 and wave troughs 172 on the distal side of the plane of opening 146. The wave line 168 is reinforced somewhat and designed in the form of a sealing lip 174 which is, therefore, located partially on the proximal side and partially on the distal side of the plane of opening 146. It is, however, apparent in a plan view, as illustrated in FIG. 6, that the sealing line 166 and, therefore, also the sealing lip 174 delimit a circular opening 176 of the sealing element 74. The opening 176 has a minimum inner diameter in a basic position, as illustrated, for example, in FIGS. 3 to 6. The opening 176 can, as illustrated, for example, in FIG. 11, be widened to such an extent that an inner diameter thereof corresponds to an inner diameter of the sealing element 74 in the area of the beads 162. The folded wall 164 unfolds at the same time, is practically completely unfolded over the entire length between the beads 162 and thus defines an essentially cylindrical wall surface.

In order to stabilize the sealing element 74, reinforcing ribs 178 are formed on an outer side of the wall 164 proceeding from the beads 164 and reach as far as the sealing lip 166. The sealing element 74 is, altogether, injection molded in one piece from a plastic material which preferably has elastomeric properties. Furthermore, two recesses 180 located diametrically opposite one another are provided on each of the flange rings 148 and are designed to correspond to two projections 182 which project in a radial direction from the sealing element holder 76 in the direction towards the longitudinal axis 12. The recesses 180 in conjunction with the projections 182 form a device for securing against rotation and so the sealing element 74 and the sealing element holder 76 cannot be rotated relative to one another about the longitudinal axis 12 in an assembly position illustrated, for example, in FIGS. 2 and 3.

After the holder ring 72 has been equipped with the cross recessed valve 70, the sealing element holder 76, into which the sealing element 74 is inserted in the manner described above, can be connected to the holder ring 72. On the distal side, an annular end face 184 of the sealing element 74, which points in a distal direction, forms a contact surface for the attachment flange 92. As a result of interlocking connection of the holder ring 72 with the sealing element holder 76 in the manner described above, the attachment flange 92 and the flange ring 148 are pressed against one another and form a perfect seal.

Four recesses 186, which are distributed uniformly over the circumference, are open in a radial direction towards the longitudinal axis 12, form connecting members and serve to accommodate corresponding connecting elements 188 of the protection device 78, are provided at least in the bead 162 on the proximal side. The protection device 78 comprises an annular base member 190 which is closed upon itself and defines a circular opening 192. An annular projection 196 protrudes from the base member 190 in a radial direction outwards, adjacent to a proximal end 194. The connecting elements 188 are arranged somewhat further to the distal side in the form of short, web-like projections. They extend over approximately ⅛ of the overall circumference of the base member 190 and are designed to correspond to the recesses 186. The base member 190 can, therefore, be mounted directly on the sealing element 74, wherein the connecting elements 188 engage in the recesses 168 in a form locking manner for this purpose. They therefore form, at the same time, a device for preventing rotation of the protection device 78 relative to the sealing element 74. Furthermore, they also form a positioning aid for the protection device 78 relative to the sealing element 74.

Figure 8:
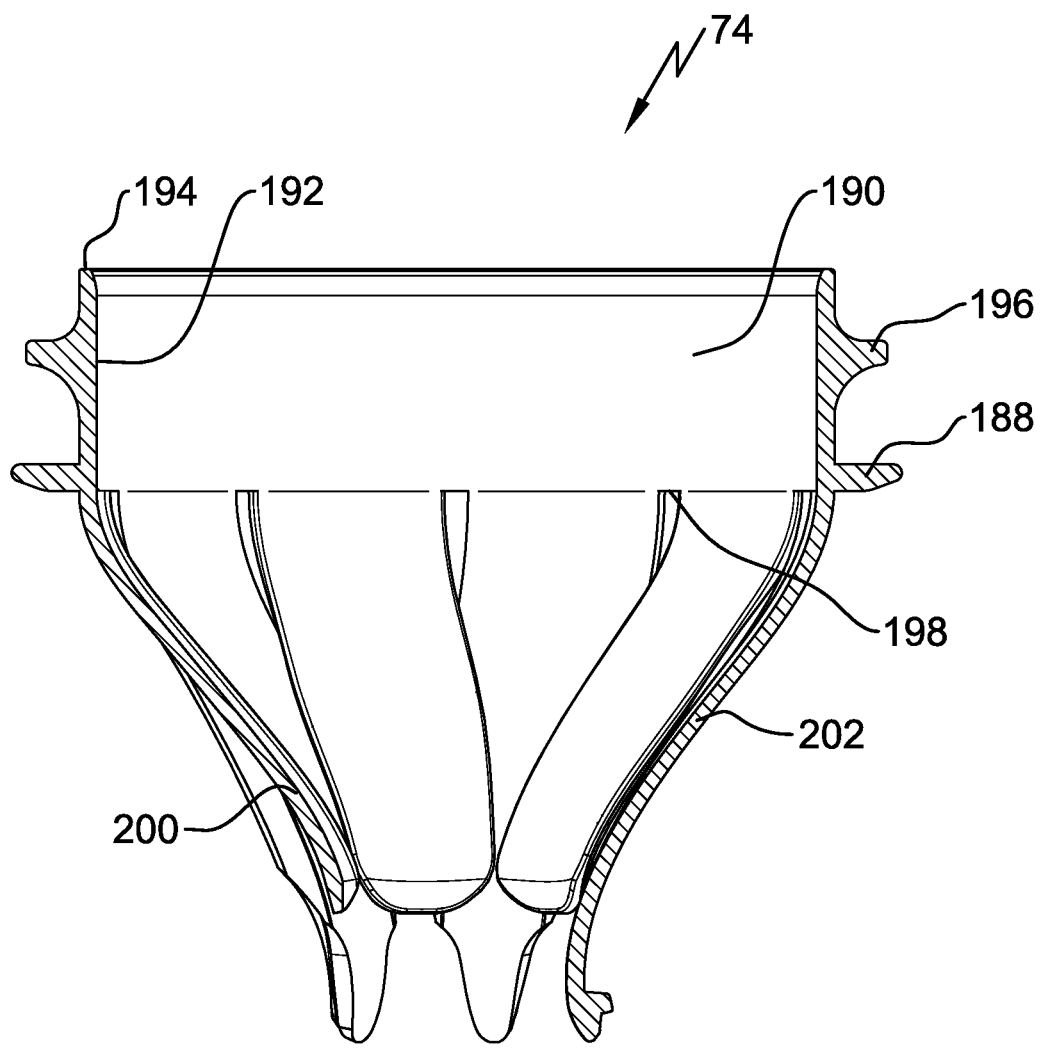
FIG. 8 shows a sectional view along line 8-8 in FIG. 7.
Figure 9:
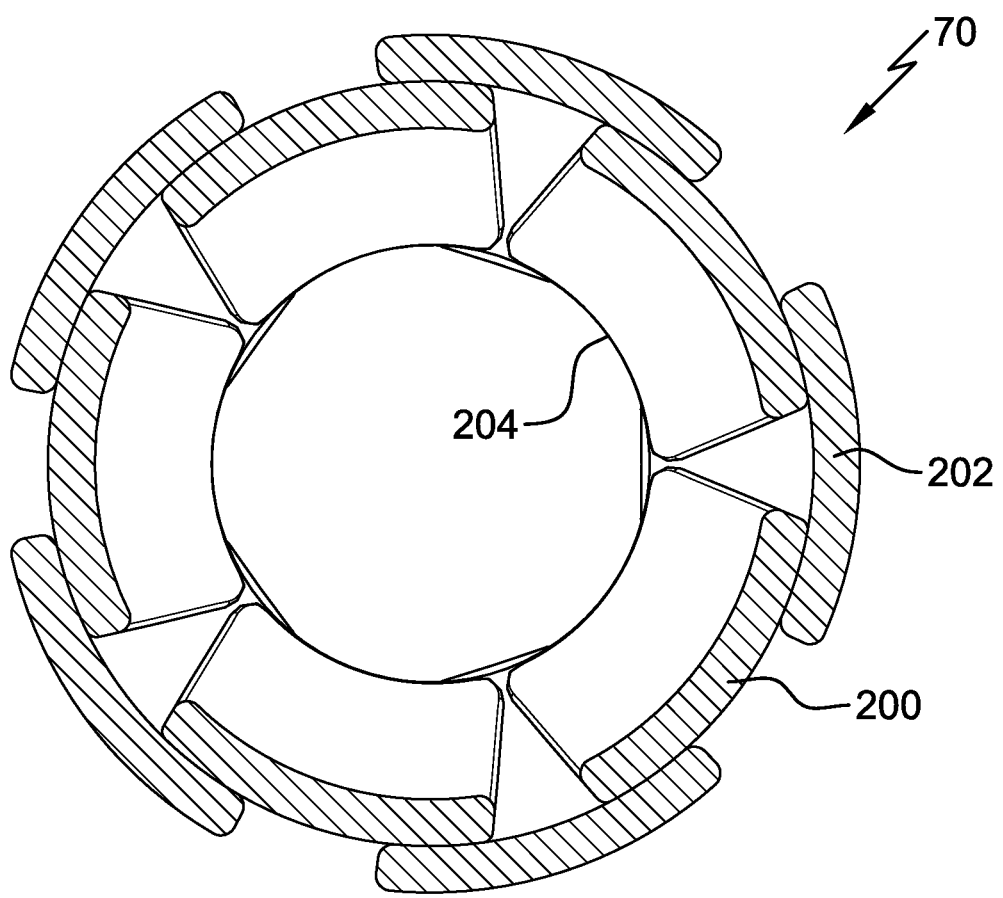
FIG. 9 shows a sectional view along line 9-9 in FIG. 7.
Figure 10:
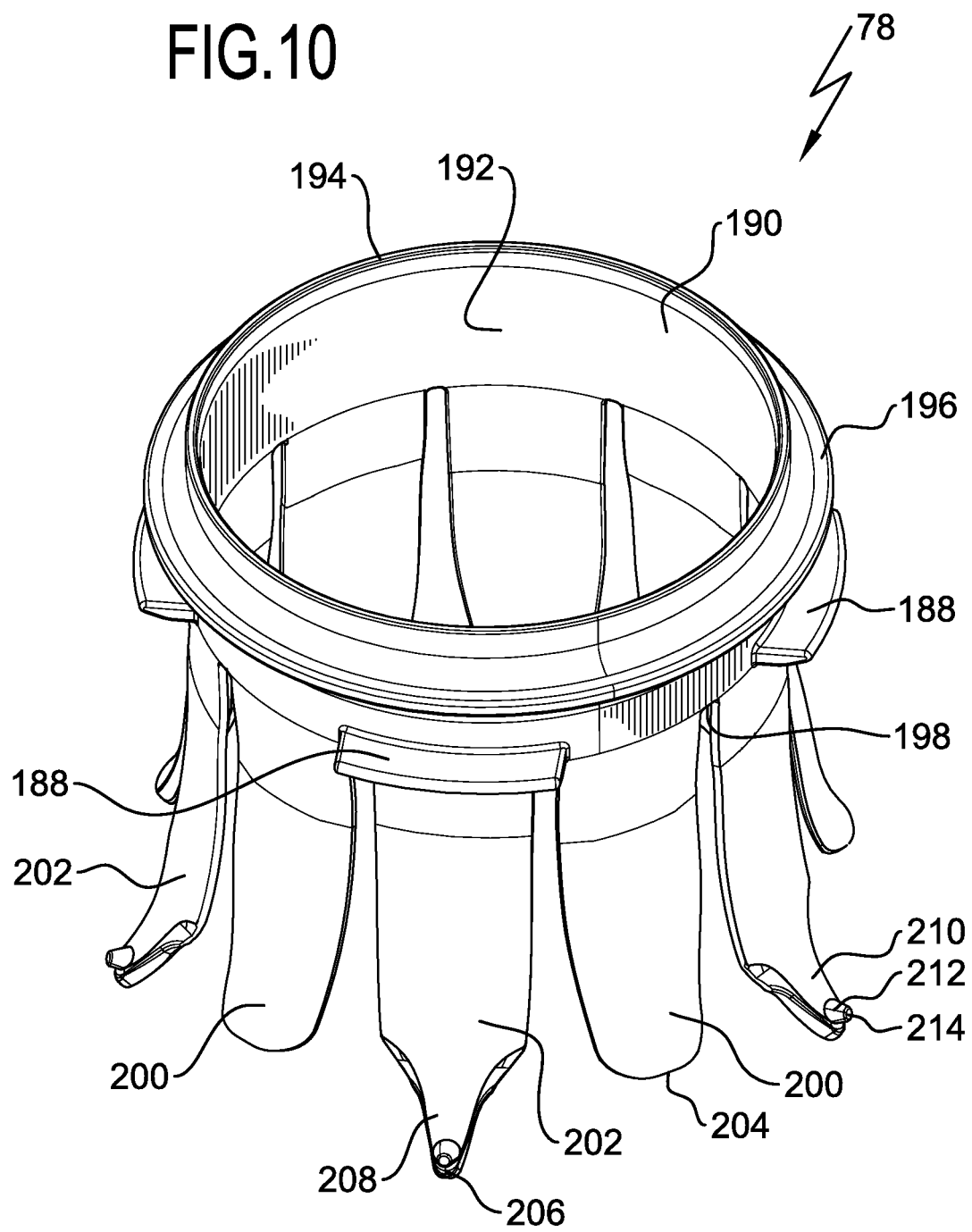
FIG. 10 shows a perspective view of the protection device in a position widened to the maximum.

A total of 10 protection elements, five tongue-like short protection elements 200 and five long protection elements 202, respectively, extend in a distal direction from an edge 198 of the base member 190 on the distal side. They have in a longitudinal section, as illustrated in FIG. 8, a thickness which is constant over their entire length. The short protection elements 200 essentially have more or less the same width up to their free ends 204, the long protection elements 202 approximately to the same length as the short protection elements 200 but then the width of the long protection elements 202 decreases considerably towards their distal end 206 and so a narrow protection element section 208 is formed which is designed, in its outer contour, to correspond essentially to a wave trough 172.

The long protection elements 202 each have a retaining element 212 which projects from an outer side 210 at an angle somewhat in a distal direction and has a length of less than 1 mm. The retaining element is essentially designed in the shape of a truncated cone and has a rounded tip 214.

Figure 7:
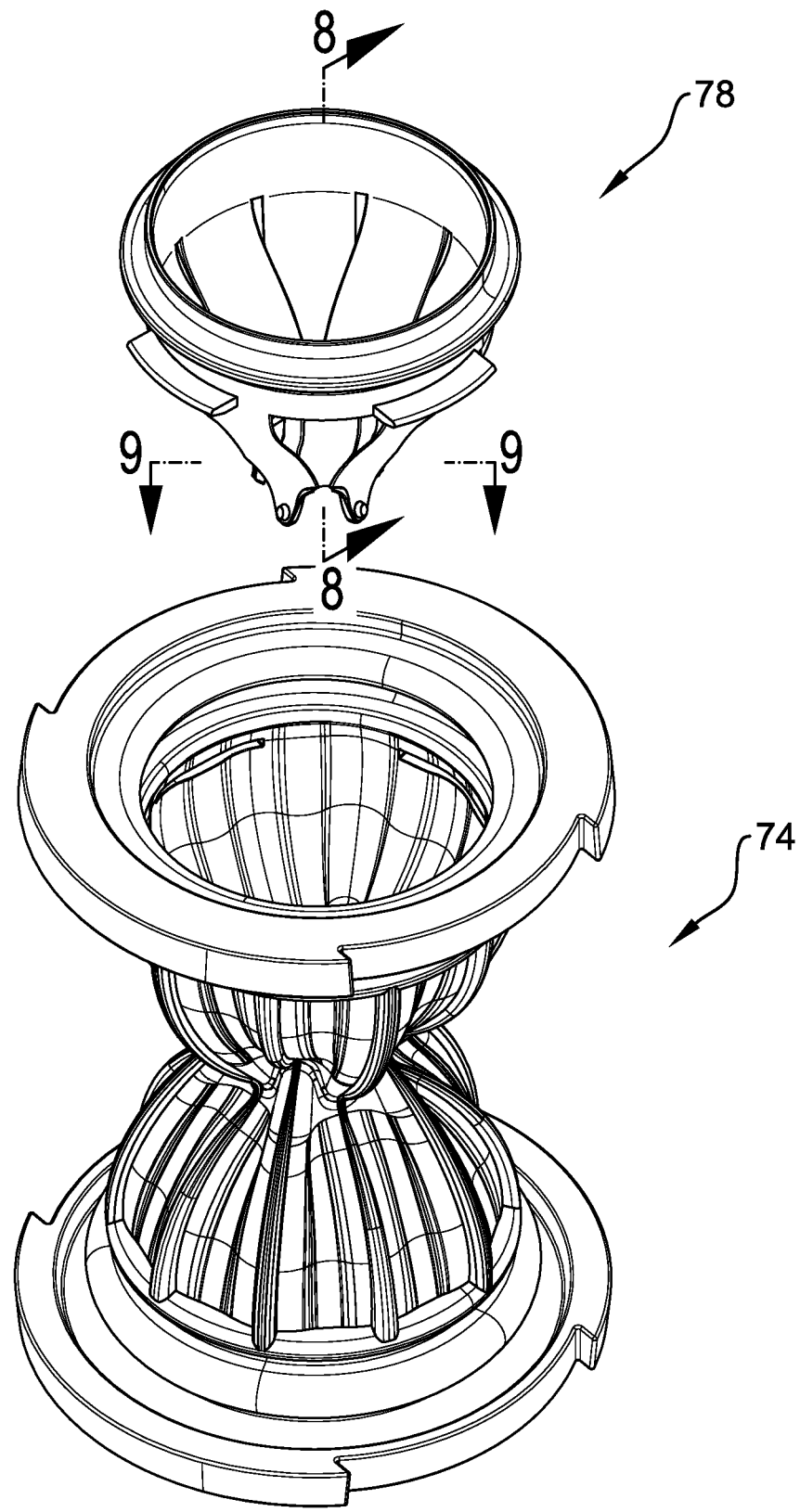
FIG. 7 shows a perspective, exploded illustration of a sealing element with protection device.

When the base member 190 is connected to the sealing element 174 in the manner described above, the protection elements 200 and 202, which are flexible on account of their slight thickness, will be folded in the direction towards the longitudinal axis 12 and take up the position illustrated in FIGS. 6 to 8. It should be noted that the long protection elements 202 extend away from the edge 198 on the distal side of the connecting elements 188, the short protection elements 200 in the areas of the edge 198, to which no connecting element 188 corresponds. As a result of the recesses 186 provided accordingly, the protection device 78 can be connected to the sealing element 74 in the correct position; this means that in a basic position all five protection element sections 208 engage in corresponding wave troughs 172. As a result, it is ensured that the distal ends 204 and 206 of the protection device 78 reach, in practice, as far as the sealing line 166 and essentially cover an inner wall surface 216 of the sealing element 74 completely.

In the assembled basic position, the protection elements 200 and 202 already project little from the wall surface 216 on the distal side of the bead 162 and touch it, at the most, close to their ends 204 and 206. In the basic position, the protection elements 200 and 202 are arranged to overlap one another, wherein the short protection elements 200 are located closer to the longitudinal axis 12 than the long protection elements 202. As a result, only the retaining elements 212 touch the wall 164 of the sealing element 74 adjacent to the sealing line 166.

If an instrument or, as illustrated, for example, in FIG. 11, the obturator 22 is inserted into the sealing element 74 from the proximal side, it comes into contact, first of all, with inner surfaces of the short protection elements 200. If an outer diameter of an instrument, as is the case for the obturator 22, is greater than the opening 176, the short protection elements 200 will be pressed against the long protection elements 202 and pivoted outwards. In this respect, the retaining elements 212 will also be pressed into the wall 164 of the sealing element 74 with their tips 214. This leads to a bulge 218 in the wall 164 due to the retaining elements 212 and so they become caught in the wall 164; it can also be said that the retaining elements 212 and the sealing element 74 are in engagement with one another. As a result of the retaining elements 212 becoming caught in the wall 164, a relative movement of the distal ends 206 of the long protection elements 202 relative to the sealing element 74 is, in practice, prevented. Irrespective of any widening or unfolding of the wall 164 as a function of a diameter of the instrument inserted, the distal ends 206 of the long protection elements 202 always reach as far as the sealing line 166 and protect the sealing element 74 from any possible damage, as described at the outset, as a result of the wall 164 coming into contact with sharp edges of the instruments inserted.

Even when a longitudinal axis of the instrument inserted is tilted somewhat relative to the longitudinal axis 12, the catching effect of the retaining elements 212 remains. As a result of a connecting device 220 formed by the recesses 186 and the connecting elements 188, any tilting of the instrument shaft, which abuts, first of all, on the protection device, will be transferred directly to the sealing element 74, namely in the area of the bead 162 and so the sealing element 74 will be tilted analogously to any tilting of the protection device 78. The special arrangement of the protection device 78 on the sealing element 74 therefore also forms, as it were, an inclination adjustment during the insertion of instruments. The first bead section 154 is suitable, in addition and in particular, for this purpose and this section allows not only a tilting movement but also a transversal movement, at least to the extent that the first bead section 154 is spaced from an inner wall of the sealing element holder 76.

As a result of the curvature of the protection elements 200 and 202 slightly convexly away from the wall 164, it is ensured that an instrument inserted can, first of all, come into contact with distal end areas of the protection elements 200 and 202 before it can touch the sealing lip 174.

The cover 80 serves to close the seal housing 16. It comprises an annular frame 222, from which a cover surface 224, which narrows conically in diameter, extends in the interior and in a distal direction as far as a cover opening 226 which defines a maximum inner diameter of the seal arrangement 20. Instruments with shaft diameters which are greater than an inner diameter of the cover opening 226 cannot be inserted into the trocar sleeve 14. The cover 80 has, in addition, two tongues 228 which point in a distal direction and are located opposite one another and, at free ends, have snap-in projections 230 which can be brought into engagement with corresponding snap-in edges on the sealing element holder 76, which are not illustrated in the Figures. The cover 80 can then be snapped onto the sealing element holder 76 in a simple manner following assembly of the sealing element holder 76 on the seal housing 16.

In order to be able to insert the trocar sleeve 14 into a human or animal body, the obturator 22 is provided. It comprises a hollow shaft 232 which extends coaxially to the longitudinal axis 12, narrows continuously in its outer diameter in a distal end area 234 and defines a rounded tip 236. The end area 234 is not designed to be circular at any point in its cross section but rather non-symmetric as a result of defined recesses 238 which extend parallel to the longitudinal axis 12. In a proximal end area 240, four holder projections 242 are provided on an outer side of the shaft 232, these projections being arranged so as to be offset respectively through 90° relative to one another and serving to mount and connect a cover 244 having essentially the shape of a semi-sphere. Corresponding projections 246 are formed on the cover 244 on an inner side. Optionally, the cover 244 can also be screwed or adhered to the shaft 232 and its holder projections 242. In addition, the tongue-like projection 250 projects from the cover 244 in a distal direction and is designed to correspond to the recess 50 so that the obturator 22 can be inserted into the trocar sleeve 14 with a defined orientation with respect to the longitudinal axis 12. If the obturator 22 is pushed completely into the trocar sleeve 14, the distal end area 234 projects beyond an end face 252 of the shaft 18 which is inclined through approximately 45° with respect to the longitudinal axis 12, as illustrated in FIG. 12.

In the interior of the seal housing 16, sealing is brought about via the sealing element 74 as well as with respect to an outer area of the sealing element holder 76 and the inner wall 144 of the trocar sleeve 14 by means of the holder sealing element 140. If the obturator 22 is removed from the trocar sleeve 14, the cross recessed valve 70 closes a channel which extends along the trocar sleeve 14 in a fluid-tight manner. On account of the outer surfaces of the valve member 96 pointing away somewhat from the longitudinal axis 12, the sectional surfaces 102 will be pressed against one another, in addition, if an overpressure is present in the interior of the body and, therefore, in the area of the shaft 18, in order to close the slits 100. As a result, in the case of laparoscopic operations, during which an overpressure is generated in the abdominal space of a patient by means of a gas in order to keep the operation site free, this overpressure can be maintained even when instruments or, for example, in an analogous manner the obturator 22 are inserted into the interior of the body by means of the trocar system 10.

It is also to be noted that the cross recessed valve 70 can only be opened by means of a distal end of an instrument or, for example, the tip 236 of the obturator 22 when, during the insertion of an instrument, its shaft, for example, the shaft 232 of the obturator 22 is sealed by means of the sealing lip 144 of the sealing element 74. It is thus ensured that either the cross recessed valve 70 will be closed or sealing be brought about by means of the sealing element 74 relative to the instrument inserted.

The trocar sleeve 14, the holder ring 72, the cross recessed valve 70, the sealing element 74, the protection device 78, the sealing element holder 76 as well as the cover 80 are each designed in one piece and preferably injection molded from a sterilizable plastic material. The obturator 22 is designed in two parts, as described, and can likewise be manufactured from a plastic material by way of injection molding.

A gas or a liquid can be introduced into or also withdrawn from the interior of a patient's body through the shaft 18 via the closure element 58 when the closing plunger 64 is in a corresponding position, even when an instrument, for example, the obturator 22 is inserted into the trocar sleeve 14 and a channel defined by the trocar sleeve 14 is sealed on the proximal side of the short connection piece 54.

What is claimed is:

1. Surgical sealing system, comprising:
a trocar with an outermost trocar sleeve,
a surgical sealing element having an insertion opening adapted to be widened, and
a surgical sealing element holder for holding the surgical sealing element,
the surgical sealing element holder having a resilient holder sealing element for sealing the surgical sealing element holder with respect to an inner sealing surface of the trocar sleeve, the holder sealing element being adapted to be pressed against the inner sealing surface of the trocar sleeve with a pretensioning force,
wherein the holder sealing element is designed in one piece with the surgical sealing element holder.

2. Surgical sealing system as defined in claim 1, wherein the holder sealing element is deformable elastically at least in sections.

3. Surgical sealing system as defined in claim 1, wherein the surgical sealing element holder is adapted to be connected detachably to the trocar sleeve.

4. Surgical sealing system as defined in claim 1, wherein the trocar sleeve has a sealing element holder receptacle for insertion of the surgical sealing element holder.

5. Surgical sealing system as defined in claim 1, wherein the holder sealing element abuts on an annular surface of the trocar sleeve pointing in a proximal direction or approximately in a proximal direction.

6. Surgical sealing system as defined in claim 1, wherein the surgical sealing element seals the insertion opening during insertion of a surgical instrument.

7. Surgical sealing system as defined in claim 1, further comprising a surgical protection device for the surgical sealing element, said protection device comprising a base member adapted to be arranged on the trocar or on a part of the trocar, the protection device being closed in a ring shape or closed approximately in a ring shape and having an opening and several protection elements arranged in circumferential direction and pointing parallel to or towards a longitudinal axis of the protection device, said protection elements having free ends pointing approximately in a distal direction, wherein at least some of the protection elements have at least one retaining element on an outer side at their free ends or in an area of their free ends for engagement with the surgical sealing element.

8. Surgical sealing system as defined in claim 7, wherein the at least one retaining element is designed in the form of a retaining projection protruding from the protection elements.

9. Surgical sealing system as defined in claim 7, wherein at least some of the retaining elements project at right angles or approximately at right angles from the protection elements or point away from the protection elements at an angle with respect to an extension of the protection elements in the area of their free ends.

10. Surgical sealing system as defined in claim 1, wherein the inner sealing surface forms an inner wall section of the trocar sleeve.

11. Surgical sealing system as defined in claim 1, wherein the holder sealing element is designed in the form of a flange projecting outward from the surgical sealing element holder in a radial direction.

12. Surgical sealing element holder for holding a surgical sealing element of a surgical sealing system comprising a trocar with an outermost trocar sleeve, said sealing element having an insertion opening adapted to be widened, the surgical sealing element holder comprising:
a holder sealing element for sealing the surgical sealing element holder with respect to an inner sealing surface of the trocar sleeve,
wherein the holder sealing element is designed in one piece with the surgical sealing element holder.

13. Surgical sealing element holder as defined in claim 12, wherein the surgical sealing element holder is designed for a detachable connection to the trocar sleeve.

14. Surgical sealing element holder as defined in claim 12, wherein the holder sealing element is designed in the form of a flange projecting from the surgical sealing element holder in a radial direction.

15. Surgical sealing element holder as defined in claim 12, wherein the flange is inclined at an angle of inclination of between 1-15 degrees in a distal direction with respect to a plane extending transversely to a longitudinal axis of the surgical sealing element holder.

16. Surgical sealing element holder as defined in claim 12, wherein the holder sealing element is deformable elastically at least in sections.

17. Surgical sealing element holder as defined in claim 12, wherein the holder sealing element has an additional seal.

18. Surgical sealing element holder as defined in claim 17, wherein the additional seal is integrally formed onto the holder sealing element.

19. Surgical sealing element holder as defined in claim 17, wherein the additional seal is produced from an elastomer.

* * * * *